United States Patent
Doan et al.

(10) Patent No.: US 8,255,062 B2
(45) Date of Patent: Aug. 28, 2012

(54) LEFT CHAMBER PRESSURE SENSOR LEAD DELIVERY SYSTEM

(75) Inventors: Phong D. Doan, Stevenson Ranch, CA (US); Dave Anderson, Castaic, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/157,173

(22) Filed: Jun. 9, 2011

(65) Prior Publication Data
US 2011/0245842 A1    Oct. 6, 2011

Related U.S. Application Data

(62) Division of application No. 11/207,669, filed on Aug. 19, 2005, now Pat. No. 7,983,765.

(51) Int. Cl.
*A61N 1/00* (2006.01)
*A61B 5/04* (2006.01)

(52) U.S. Cl. ........ 607/116; 607/117; 607/126; 607/128; 600/373

(58) Field of Classification Search .......... 607/116–117, 607/122, 126; 600/373
See application file for complete search history.

(56) References Cited

U.S. PATENT DOCUMENTS

| | | |
|---|---|---|
| 4,578,076 A | 3/1986 | Luukkainen et al. |
| 4,628,944 A | 12/1986 | MacGregor et al. |
| 4,712,555 A | 12/1987 | Thornander et al. |
| 4,788,980 A | 12/1988 | Mann et al. |
| 4,940,052 A | 7/1990 | Mann et al. |
| 4,944,298 A | 7/1990 | Sholder |
| 5,010,894 A | 4/1991 | Edhag |
| 5,466,254 A | 11/1995 | Helland |
| 5,476,483 A | 12/1995 | Bornzin et al. |
| 5,545,206 A | 8/1996 | Carson |
| 5,824,032 A | 10/1998 | Belden |
| 6,328,699 B1 | 12/2001 | Eigler et al. |
| 6,512,958 B1 | 1/2003 | Swoyer et al. |
| 6,512,959 B1 | 1/2003 | Gomperz et al. |
| 6,611,710 B2 | 8/2003 | Gomperz et al. |
| 6,638,231 B2 | 10/2003 | Govari et al. |
| 6,643,546 B2 | 11/2003 | Mathis et al. |
| 6,652,464 B2 | 11/2003 | Schwartz et al. |
| 6,671,550 B2 | 12/2003 | Iaizzo et al. |
| 6,733,500 B2 | 5/2004 | Kelley et al. |
| 6,746,404 B2 | 6/2004 | Schwartz |
| 6,783,499 B2 | 8/2004 | Schwartz |

(Continued)

FOREIGN PATENT DOCUMENTS

EP    0085967 B1    7/1986

(Continued)

OTHER PUBLICATIONS

NonFinal Office Action, mailed Jan. 9, 2008—Parent U.S. Appl. No. 11/207,669.

(Continued)

*Primary Examiner* — Nicole F Lavert

(57) ABSTRACT

An apparatus for and method of measuring pressure through a septum in a patient's heart. A lead inserted into the right side of a heart is routed through the septum to gain access to the left side of the heart. The lead includes a mounting mechanism that secures the lead to one or both sides of the septal walls. The lead also includes one or more sensors for measuring cardiac pressure on the left side of the heart and, as necessary, the right side of the heart.

1 Claim, 14 Drawing Sheets

U.S. PATENT DOCUMENTS

| | | |
|---|---|---|
| 7,218,972 B2 | 5/2007 | Rodriguez |
| 2002/0077556 A1 | 6/2002 | Schwartz |
| 2002/0077671 A1 | 6/2002 | Govari et al. |
| 2003/0050681 A1* | 3/2003 | Pianca et al. .............. 607/125 |
| 2003/0195600 A1 | 10/2003 | Tronnes et al. |
| 2004/0116992 A1 | 6/2004 | Wardle et al. |
| 2004/0147969 A1* | 7/2004 | Mann et al. .............. 607/17 |
| 2004/0220637 A1 | 11/2004 | Zdeblick et al. |
| 2004/0230281 A1 | 11/2004 | Heil et al. |
| 2004/0249429 A1 | 12/2004 | Tadlock |
| 2004/0260371 A1 | 12/2004 | Greenland et al. |
| 2005/0038491 A1 | 2/2005 | Haack |
| 2005/0060014 A1 | 3/2005 | Swoyer et al. |
| 2005/0085883 A1 | 4/2005 | Ollivier et al. |

FOREIGN PATENT DOCUMENTS

| | | |
|---|---|---|
| EP | 1266606 A2 | 12/2002 |
| EP | 1266606 A3 | 5/2003 |
| EP | 1216653 B1 | 4/2005 |
| EP | 1053762 B1 | 8/2005 |
| EP | 1264572 B1 | 8/2005 |
| EP | 1216655 B1 | 2/2006 |
| EP | 1216652 B1 | 6/2007 |

OTHER PUBLICATIONS

NnoFinal Office Action, mailed Aug. 20, 2008—Parent U.S. Appl. No. 11/207,669.

NonFinal Office Action, mailed Jan. 30, 2009—Parent U.S. Appl. No. 11/207,669.

Final Office Action, mailed Jul. 15, 2009—Parent U.S. Appl. No. 11/207,669.

Final Office Action, mailed Oct. 21, 2009—Parent U.S. Appl. No. 11/207,669.

NonFinal Office Action, mailed Jan. 22, 2010—Parent U.S. Appl. No. 11/207,669.

NonFinal Office Action, mailed Jul. 21, 2010—Parent U.S. Appl. No. 11/207,669.

Final Office Action, mailed Dec. 30, 2010—Parent U.S. Appl. No. 11/207,669.

Notice of Allowance, mailed May 17, 2011—Parent U.S. Appl. No. 11/207,669.

* cited by examiner

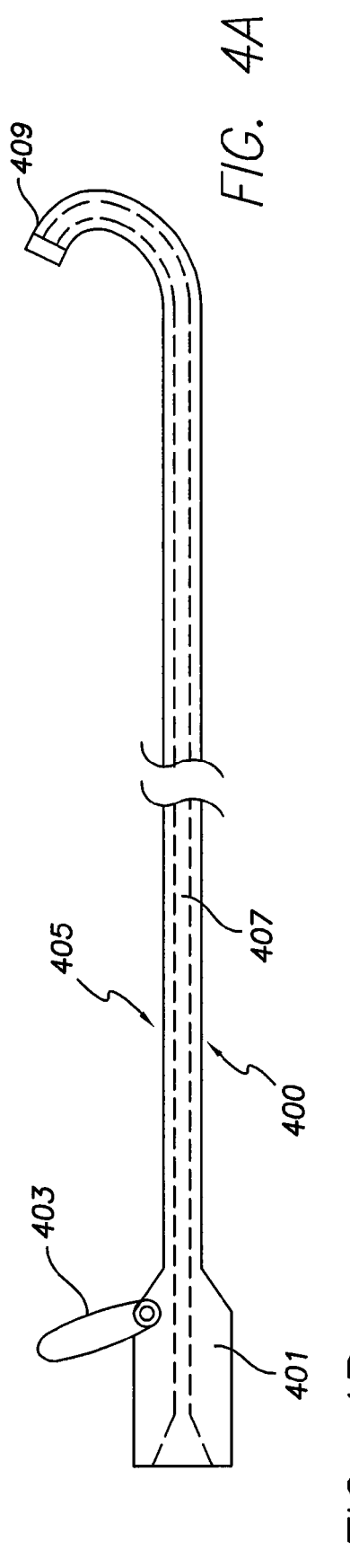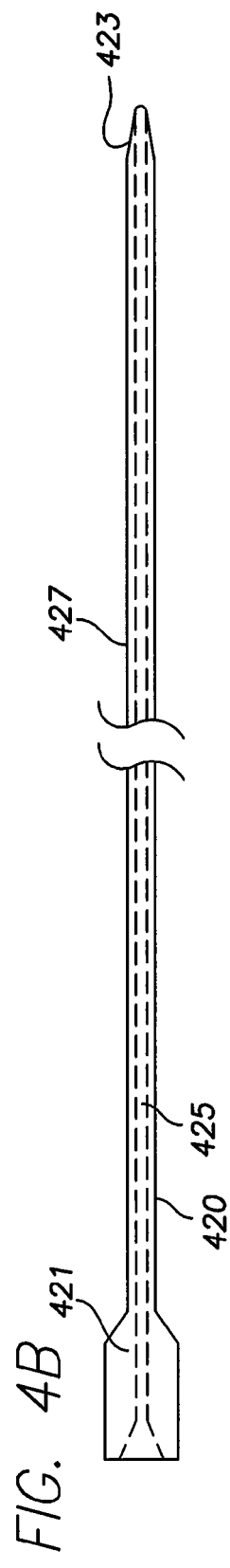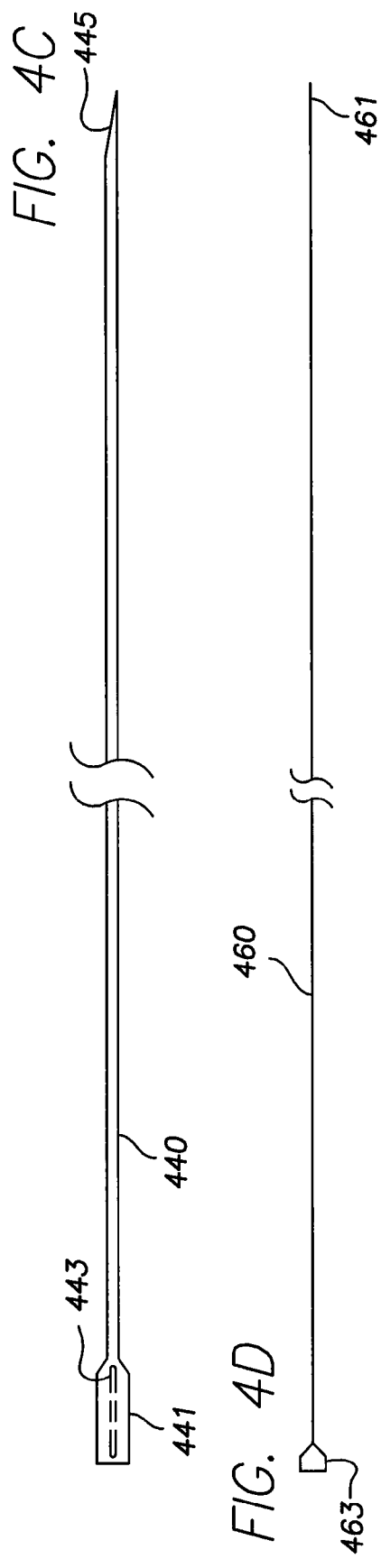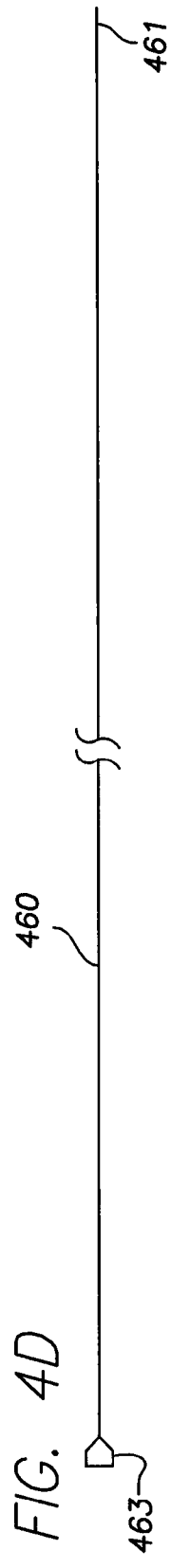

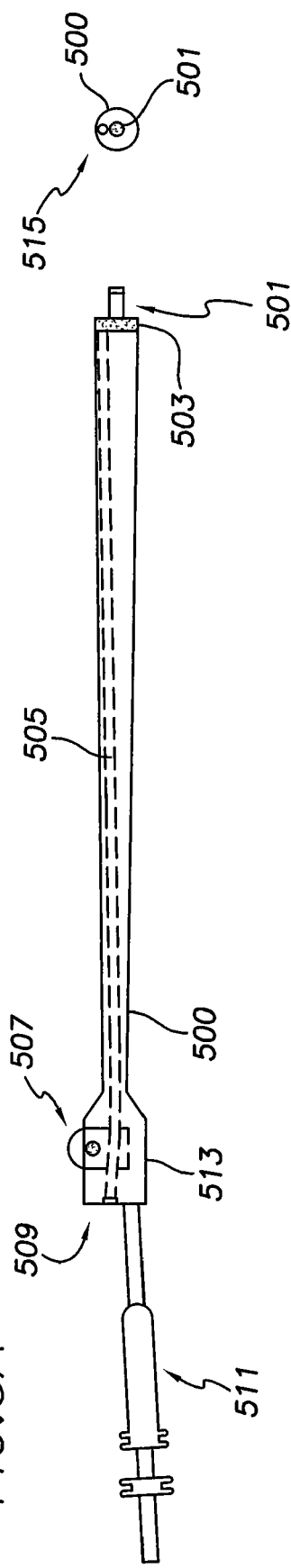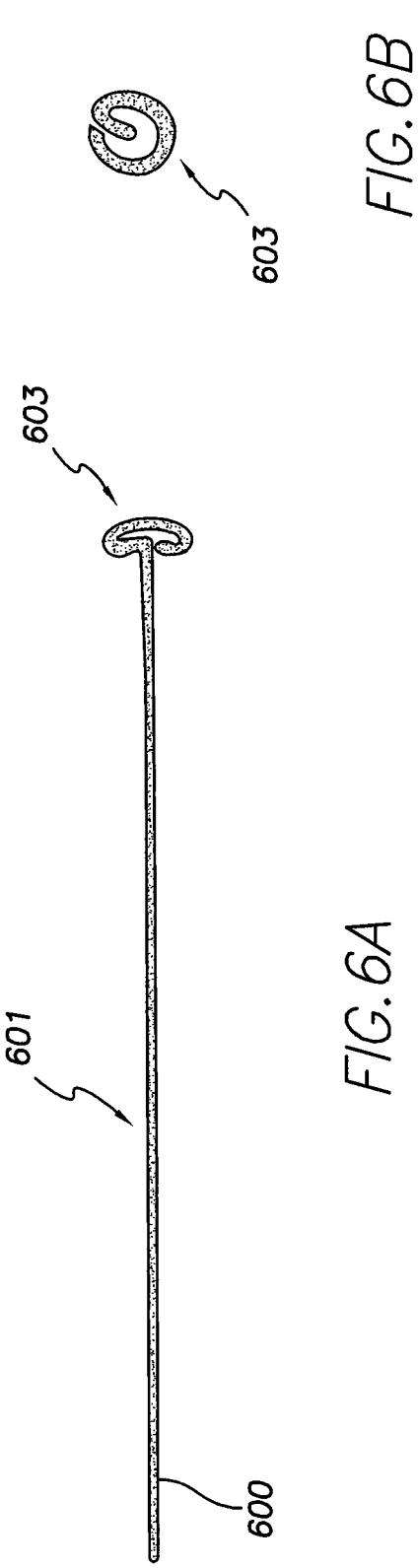

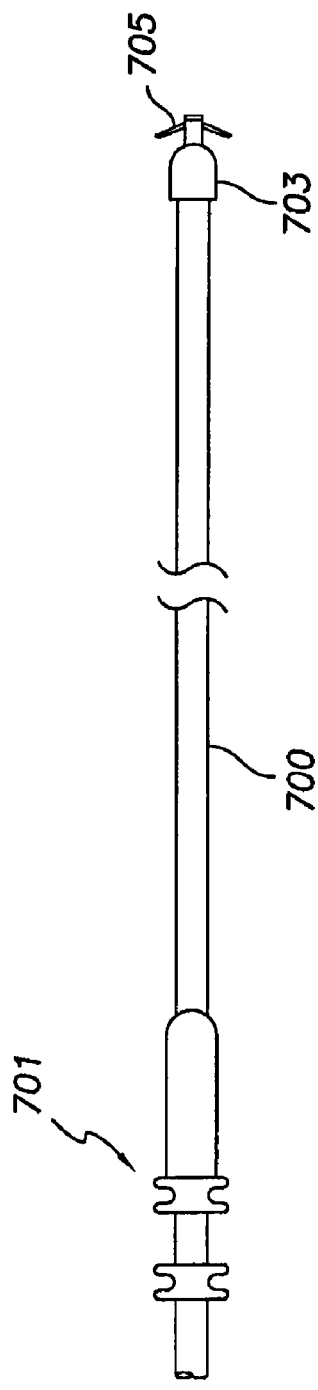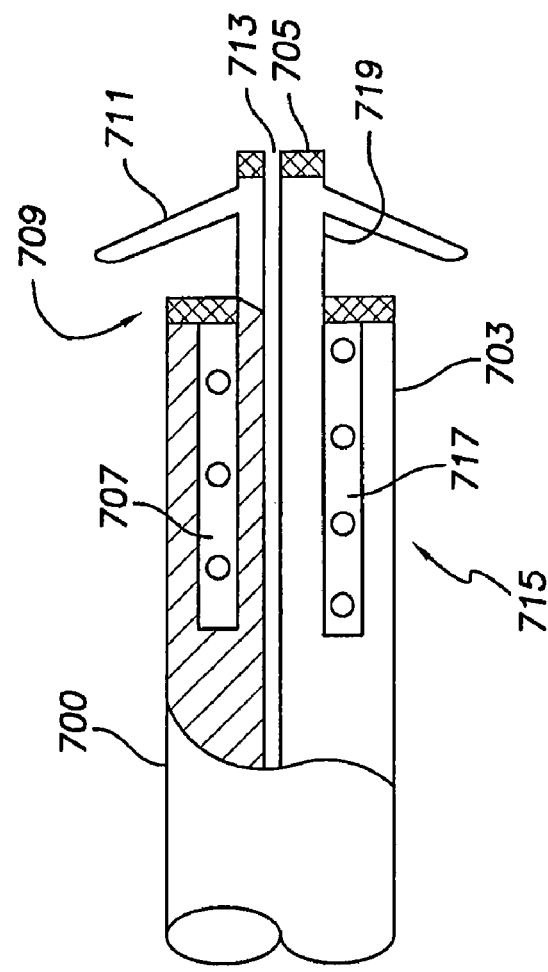
FIG. 7A
FIG. 7B

LEFT CHAMBER PRESSURE SENSOR LEAD DELIVERY SYSTEM

CROSS REFERENCE TO RELATED APPLICATIONS

This application is a division of U.S. patent application Ser. No. 11/207,669, filed Aug. 19, 2005, titled "Left Chamber Pressure Sensor Lead Delivery System," now U.S. Pat. No. 7,983,765.

FIELD OF THE INVENTION

This application relates generally to implantable cardiac stimulation devices and, more specifically, to a lead system implanted through a septal wall.

BACKGROUND OF THE INVENTION

When a person's heart does not function normally due to, for example, a genetic or acquired condition various treatments may be prescribed to correct or compensate for the condition. For example, pharmaceutical therapy may be prescribed for a patient or a pacemaker may be implanted in the patient to improve the operation of the patient's heart.

In conjunction with such therapy it may be desirable to measure pressure in one or more chambers of the heart. For example, absolute cardiac pressure may be used as an indicator for several potentially lethal cardiac conditions. By measuring cardiac pressure, abnormal conditions such as these may be detected and in some cases the patient's therapy may be modified to compensate for the abnormal conditions. As an example, if cardiac pressure is continuously measured, the operation of an implanted device such as a pacemaker may be adjusted, as necessary, according to conditions diagnosed as a result of the pressure measurements.

Conventionally, pressure sensing devices have been used to measure pressures on the right side of the heart. However, measurements of right side pressure may not provide sufficient indications for detection of conditions such as congestive heart failure, hypertension and mitral valve defects. In particular, left atrial pressure has been identified as an excellent indicator for left ventricular failure.

Obtaining pressure measurements from the left side of the heart presents several challenges. First, access to the left side of the heart must be provided in a safe manner. In addition, the pressure sensors need to be implanted in a manner that ensures accurate pressure measurements may be made. Again, the use of a safe implantation technique is a primary consideration. Accordingly, a need exists for improved structures and techniques for measuring cardiac pressure.

SUMMARY

What is described herein is an apparatus for and method of measuring pressure in a chamber on the left side of a patient's heart. Access to the left chamber may be gained through a wall in the heart.

In some embodiments a lead includes a sensor and a mounting mechanism on a distal end. The distal end of the lead may be routed from a right side of the heart through a hole in a wall to the left side of the heart. At least a portion of the mounting mechanism and the sensor may thereby be positioned in the left side of the heart.

In some embodiments the distal end of a lead is routed to the left side of the heart via a guidewire. In these embodiments the lead may comprise a lumen for the guide wire.

In some embodiments a mounting mechanism comprises a set of tines. The tines may, for example, extend from a distal portion of a lead. In some embodiments the tines are positioned against a wall on the left side of the heart.

In some embodiments a mounting mechanism comprises a guidewire with a distal end that is adapted to be positioned against a wall on the left side of the heart. In some embodiments provisions may be made to prevent the guidewire from moving relative to the lead once the lead is fully implanted.

In some embodiments the lead includes a biasing mechanism on a distal end. The biasing mechanism may be adapted to press the mounting mechanism against the left side of the wall.

In some embodiments a dilator may be used to dilate the hole in the wall. The dilator may have a head portion and a body portion where the diameter of the head portion is larger than the diameter of the body portion.

These and other features, aspects and advantages of the invention will be more fully understood when considered with respect to the following detailed description, appended claims and accompanying drawings.

BRIEF DESCRIPTION OF THE DRAWINGS

Embodiments of the invention are illustrated by way of example and not by way of limitation in the figures of the accompanying drawings in which like references indicate similar elements. It should be noted that references to "an" or "one" embodiment in this discussion are not necessarily to the same embodiment, and such references mean at least one.

FIG. 4A is a diagram of one embodiment of a deflectable catheter.

FIG. 4B is a diagram of one embodiment of a dilator.

FIG. 4C is a diagram of one embodiment of a trans-septal needle.

FIG. 4D is a diagram of one embodiment of a guidewire.

FIG. 5A is a diagram of one embodiment of a lead.

FIG. 5B is a diagram of an end view of one embodiment of a lead.

FIG. 6A is a diagram of another embodiment of a guidewire.

FIG. 6B is a diagram of an end view of one embodiment of a guidewire.

FIG. 7A is a diagram of one embodiment of a lead.

FIG. 7B is a diagram of a partial cut-away view of one embodiment of a distal end of a lead.

Figure 1:
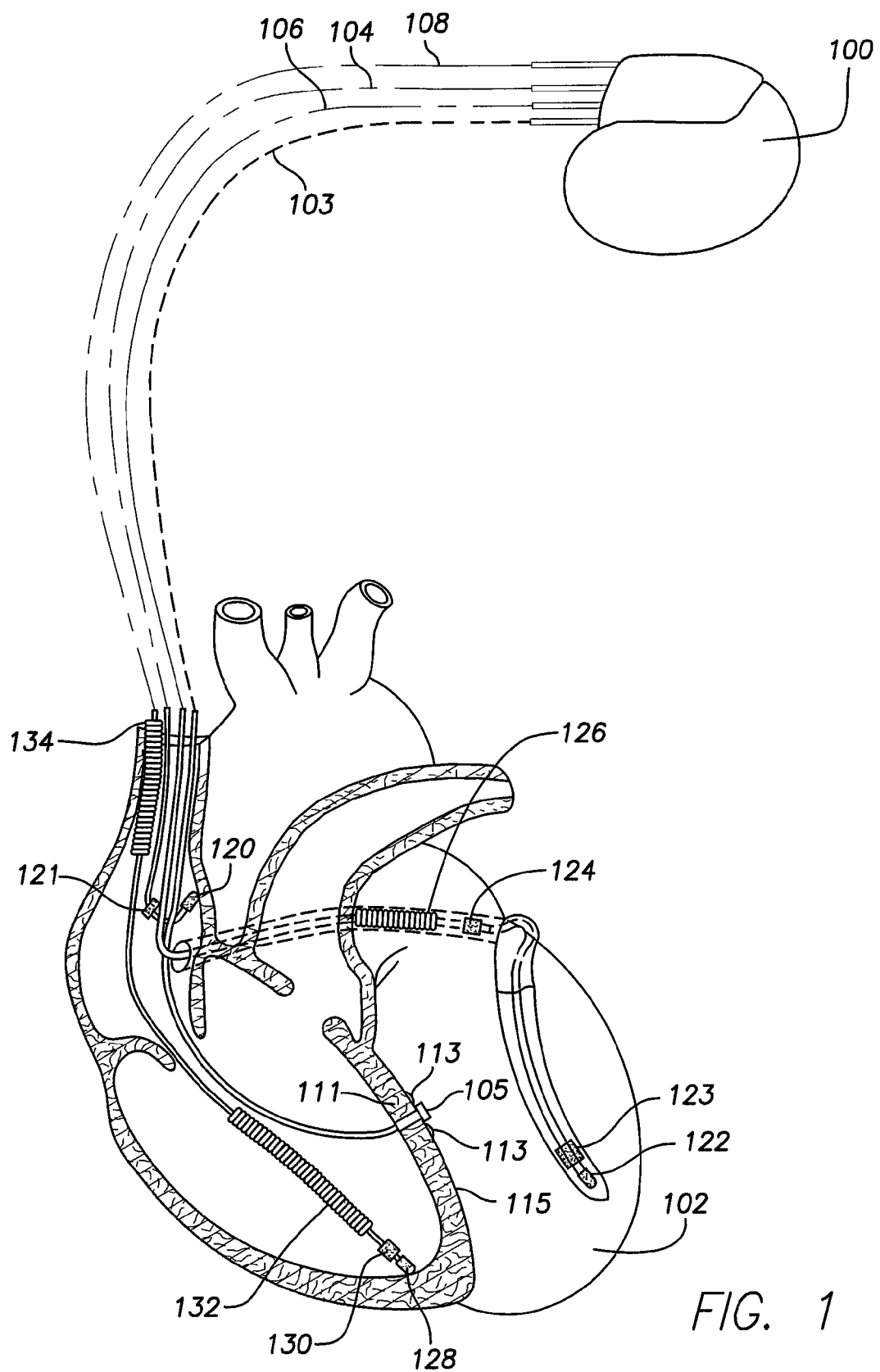
FIG. 1 is a simplified diagram of one embodiment of an implantable stimulation device in electrical communication with several leads implanted in a patient's heart for measuring pressure and delivering multi-chamber stimulation and shock therapy in accordance with the invention.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Also, like reference numerals denote like features throughout the specification and figures.

DETAILED DESCRIPTION

The invention is described below, with reference to detailed illustrative embodiments. It will be apparent that the invention may be embodied in a wide variety of forms, some of which may be quite different from those of the disclosed embodiments. Consequently, the specific structural and functional details disclosed herein are merely representative and do not limit the scope of the invention.

Referring to FIG. 1, in one aspect the invention relates to an implantable cardiac device that includes one or more leads (e.g., lead 103) that are implanted in a patient. The lead 103 consists of a lead body and includes at least one sensor 105 for measuring pressure in the patient's heart. The implantable cardiac device includes circuitry (e.g., in a stimulation device 100) that processes signals from the sensor 105 to determine relative cardiac pressure.

Figure 3:
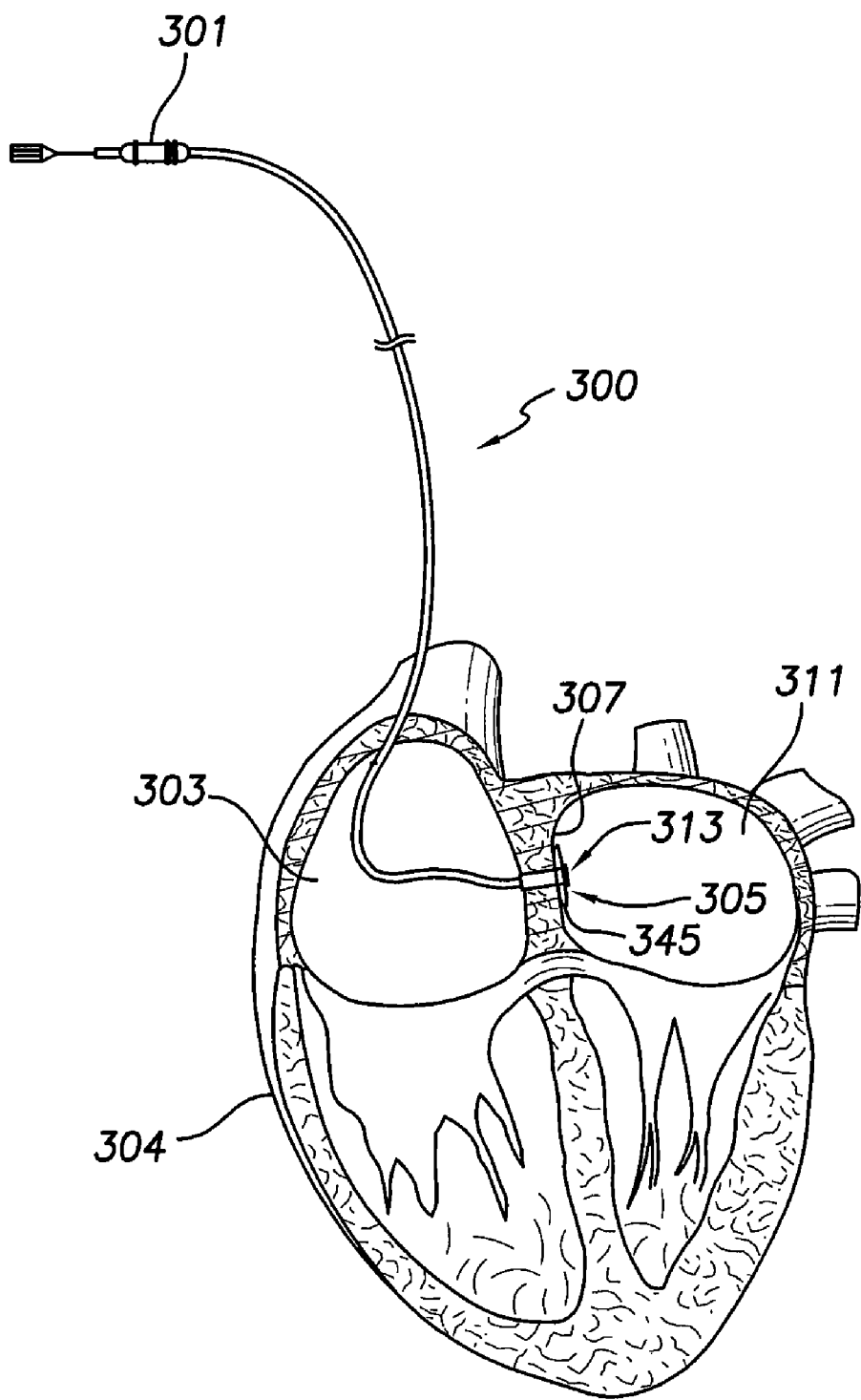
FIG. 3 is a simplified diagram of one embodiment of a cardiac lead having a sensor and a mounting mechanism that is implanted through a septum.

In embodiments where the lead is initially routed into the right side of the heart, pressure may be measured in the left side of the heart (e.g., the left atrium, left ventricle or aorta) by routing the lead through a wall in the heart (e.g., the ventricular septum 111 or the atrial septum 307 shown in FIG. 3). For example, a hole may be created in the septum by piercing the septum using a piercing device such as a needle.

After a distal portion of the lead 103 is maneuvered through the septum 111, a mounting mechanism 113 that expands from the lead 103 is positioned against a wall 115 on the left side of the septum 111. A mounting mechanism may take many forms including, for example, one or more tines or a portion of a guidewire. Additional details of an exemplary stimulation device 100 and associated leads will be discussed in conjunction with FIGS. 1 and 2.

The following description sets forth but one exemplary stimulation device that is capable of being used in connection with the various embodiments that are described below. It is to be appreciated and understood that other stimulation devices, including those that are not necessarily implantable, can be used and that the description below is given, in its specific context, to assist the reader in understanding, with more clarity, the inventive embodiments described herein.

FIG. 1 shows an exemplary stimulation device 100 in electrical communication with a patient's heart 102 by way of three leads 104, 106, and 108, suitable for delivering multichamber stimulation and shock therapy. To sense atrial cardiac signals and to provide right atrial chamber stimulation therapy, stimulation device 100 is coupled to an implantable right atrial lead 104 having, for example, an atrial tip electrode 120, which typically is implanted in the patient's right atrial appendage or septum. FIG. 1 shows the right atrial lead 104 as having an optional atrial ring electrode 121.

To sense left atrial and ventricular cardiac signals and to provide left chamber pacing therapy, stimulation device 100 is coupled to a coronary sinus lead 106 designed for placement in the coronary sinus region via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 106 is designed to receive atrial and ventricular cardiac signals and to deliver left ventricular pacing therapy using, for example, a left ventricular tip electrode 122, left ventricular ring electrode 123, left atrial pacing therapy using, for example, a left atrial ring electrode 124, and shocking therapy using, for example, a left atrial coil electrode 126 (or other electrode capable of delivering a shock). For a complete description of a coronary sinus lead, the reader is directed to U.S. Pat. No. 5,466,254, "Coronary Sinus Lead with Atrial Sensing Capability" (Helland), which is incorporated herein by reference.

Stimulation device 100 is also shown in electrical communication with the patient's heart 102 by way of an implantable right ventricular lead 108 having, in this implementation, a right ventricular tip electrode 128, a right ventricular ring electrode 130, a right ventricular (RV) coil electrode 132 (or other electrode capable of delivering a shock), and superior vena cava (SVC) coil electrode 134 (or other electrode capable of delivering a shock). Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle.

Figure 2:
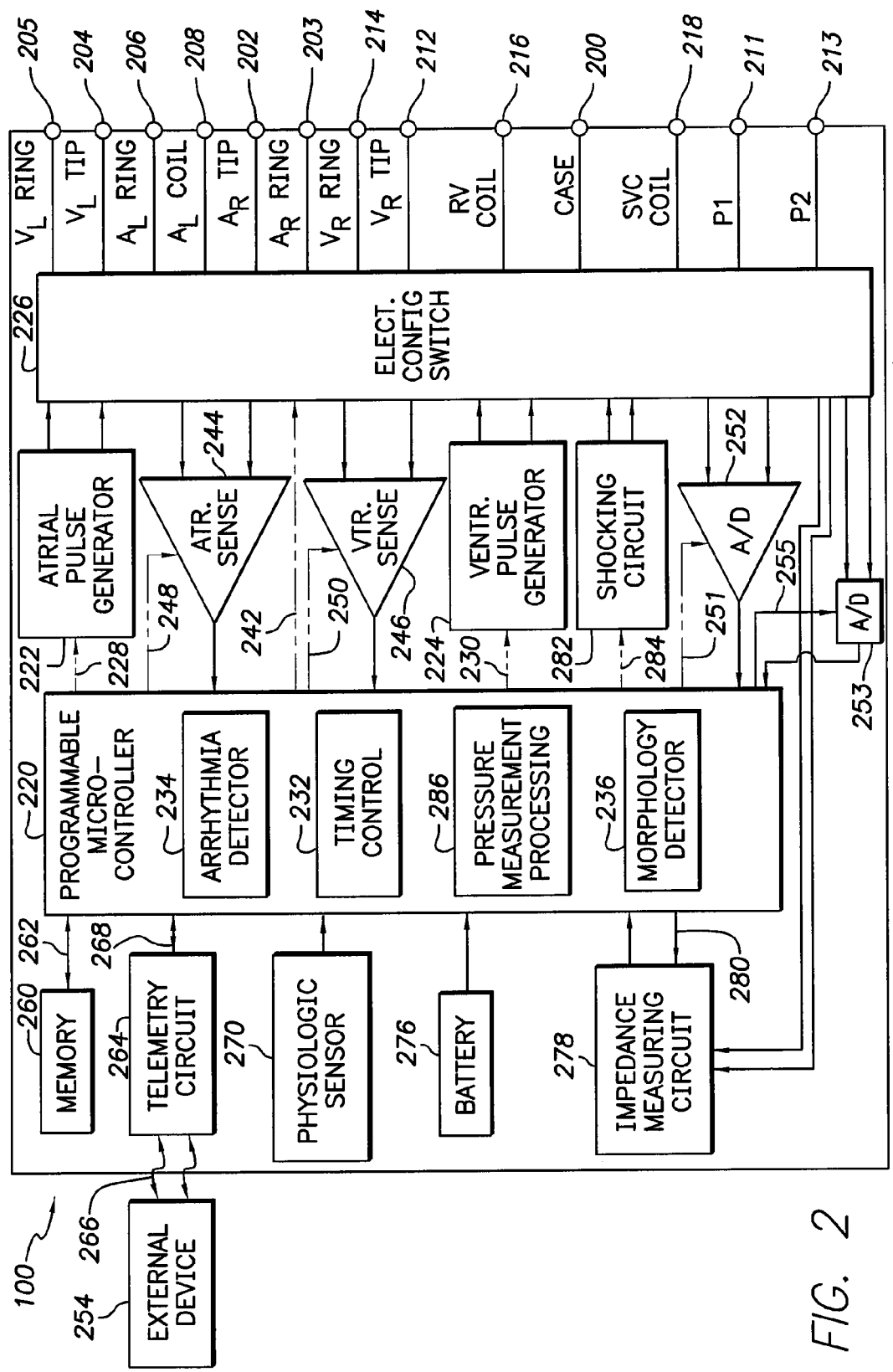
FIG. 2 is a simplified functional block diagram of one embodiment of a multi-chamber implantable stimulation device constructed in accordance with the invention, illustrating basic elements that are configured to provide pressure sensing, cardioversion, defibrillation or pacing stimulation or any combination thereof.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) with cardioversion, defibrillation, and pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 203, 204, 205, 206, 208, 211, 212, 213, 214, 216, and 218 (shown schematically and, for convenience, the names of the electrodes to which they are connected are shown next to the terminals).

To achieve right atrial sensing and pacing, the connector includes, for example, a right atrial tip terminal (AR TIP) 202 adapted for connection to the atrial tip electrode 120. A right atrial ring terminal (AR RING) 203 may also be included adapted for connection to the atrial ring electrode 121. To achieve left chamber sensing, pacing, and shocking, the connector includes, for example, a left ventricular tip terminal (VL TIP) 204, left ventricular ring terminal (VL RING) 205, a left atrial ring terminal (AL RING) 206, and a left atrial shocking terminal (AL COIL) 208, which are adapted for connection to the left ventricular tip electrode 122, the left atrial ring electrode 124, and the left atrial coil electrode 126, respectively.

To support right chamber sensing, pacing, and shocking, the connector further includes a right ventricular tip terminal (VR TIP) 212, a right ventricular ring terminal (VR RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of stimulation therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234, a morphology detector 236, and optionally an orthostatic compensator and a minute ventilation (MV) response module, the latter two are not shown in FIG. 2. These components can be utilized by the stimulation device 100 for determining desirable times to administer various therapies, including those to reduce the effects of orthostatic hypotension. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, combipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 utilizes the atrial and ventricular sensing circuits, 244 and 246, to sense cardiac signals to determine whether a rhythm is physiologic or pathologic. In reference to arrhythmias, as used herein, "sensing" is reserved for the noting of an electrical signal or obtaining data (information), and "detection" is the processing (analysis) of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to inputs of an analog-to-digital (A/D) data acquisition system 252. The data acquisition system 252 is configured (e.g., via signal line 251) to acquire intracardiac electrogram signals, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample cardiac signals across any pair of desired electrodes.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms and status information relating to the operation of the device 100 (as contained in the microcontroller 220 or memory 260) to be sent to the external device 254 through an established communication link 266.

The stimulation device 100 can further include a physiologic sensor 270, commonly referred to as a "rate-responsive" sensor because it is typically used to adjust pacing stimulation rate according to the exercise state of the patient. However, the physiologic sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses. While shown as being included within the stimulation device 100, it is to be understood that the physiologic sensor 270 may also be external to the stimulation device 100, yet still be implanted within or carried by the patient. Examples of physiologic sensors that may be implemented in device 100 include known sensors that, for example, sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), issued Dec. 19, 1995, which patent is hereby incorporated by reference.

More specifically, the physiologic sensors 270 optionally include sensors to help detect movement and minute ventilation in the patient. The physiologic sensors 270 may include a position sensor and/or a minute ventilation (MV) sensor to sense minute ventilation, which is defined as the total volume of air that moves in and out of a patient's lungs in a minute. Signals generated by the position sensor and MV sensor are passed to the microcontroller 220 for analysis in determining whether to adjust the pacing rate, etc. The microcontroller 220 monitors the signals for indications of the patient's position and activity status, such as whether the patient is climbing upstairs or descending downstairs or whether the patient is sitting up after lying down.

The stimulation device additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 µA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected. Accordingly, the device 100 preferably employs lithium or similar battery technology.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through, for example, two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, and/or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In some embodiments device 100 also may include circuitry for processing signals from one or more pressure sensors. Depending upon the application, the pressure sensors may be implanted in the heart, in other locations in the patient such as the thoracic cavity, anywhere along a lead or within the housing 200.

A typical pressure sensor generates electrical signals indicative of changes in a sensed pressure. Thus, one or more wires may be used to connect a sensor to the device 100. FIG. 2 illustrates an embodiment where two pressure signals P1 and P2 are coupled to the device 100 via terminals 211 and 213, respectively. An analog-to-digital (A/D) data acquisition system 253 may be configured (e.g., via signal line 255) to acquire and amplify the signals P1 and P2, convert the raw analog data into a digital signal, filter the signals and store the digital signals for later processing by, for example, a pressure measurement processing component 286 and/or telemetric transmission to an external device 254. Referring now to FIGS. 3-22, various embodiments of leads that may be used to measure pressure across a septal wall will be discussed.

FIG. 3 is a diagram of one embodiment of a lead 300 having a sensor 313 implanted into a left atrium 311 through a septal wall 307 (the atrial septum in this example) of the heart 309. In one embodiment, the lead 300 includes a proximal end with a housing 301 that may enclose one or more electrical contacts, openings to lumens or other components and structures. The housing 301 may be formed as a connector to allow the lead 300 to be connected to an implantable device (e.g., stimulation device 100). The electrical contacts may be coupled to electrical conductors such as wires that run the length of the lead 300. For example, the conductors may connect to the sensor 313. The lead 300 may include one or more lumens that run the length of the lead 300 or over a portion of the length of the lead 300. The lumens may house the electrical conductors, removable guidewires and other components.

In one embodiment, the lead 300 may reach the heart of the patient intravenously. The lead 300 may be partially disposed in a vein of a patient that leads to the right atrium. The distal end of the lead 300 may be partially disposed in the right atrium 303 of the heart 309 with a tip 305 (e.g., the distal end) of the lead 300 in the left atrium 311. The tip 305 of lead 300 may include a sensor 313. The sensor 313 may detect the fluid pressure in the left atrium 311.

In one embodiment, the tip 305 of the lead 300 may be situated through the septal wall 307 in the region of the fossa ovalis. The fossa ovalis is typically the thinnest section of the atrial septal wall 307. The tip 305 may be held in place by a mounting mechanism 315. The mounting mechanism 315 and installation of the lead into a patient is discussed in greater detail below. Through the use of the mounting structure, the sensor 313 may be surely fastened to the heart so that the sensor 313 may provide accurate pressure measurements from the left atrium 311.

In one embodiment, the portion 305 of the lead 300 situated in the left atrium 311 may be designed to have a relatively low profile against the septal wall 307. In this way, problems associated with protruding objects inside of the heart 309 may be avoided. For example, blood clots may form on an object that protrudes from a wall of the heart 309. If these blood clots break loose in the left side of the heart the blood clots may travel to other areas of the body such as the brain and cause a blockage in a blood vessel (i.e., an embolism).

If a structure in the heart 309 has a low profile against a wall of the heart 309, the body may quickly build up a biological layer of endothelial cells ("the intima") over the structure. As a result, the likelihood of blood clots breaking loose may be significantly reduced as compared to structures that protrude relatively deeply into the left side of the heart. The buildup of the intima also may assist in firmly attaching a mounting mechanism to the septal wall 307. As a result, the mounting mechanism may be attached to the heart 309 in a sufficiently stable manner so as to prevent injury to the heart 309. The lead tip 305, sensor 313 and mounting mechanism 315 have a low profile to diminish the problem of blood clots and to take advantage of intima build up to secure the sensor 313 in the left atrium 311.

In one embodiment, the lead 300 provides a secure and safe attachment to the septal wall 307 that may be used in combination with other leads and sensors implanted in the patient, by an external monitoring device to provide a variety of pressure measurements in real time. These cardiac pressure measurements may provide valuable information for diagnosing a variety of cardiac problems. Examples of cardiac problems that may be associated high pressure measurements in the left atrium 311 include mitral stenosis and left ventricle failure. When diagnoses such as these are used in conjunction with a heart stimulation device, appropriate therapy such as cardiac resynchronization therapy may be immediately delivered to the patient.

In another embodiment, the lead 300 may have additional sensors placed throughout the length of the lead 300. For example, a sensor may be placed in the body of the lead 300 such that it would be positioned in the right atrium 303 or in other structures of the heart 309 when the tip is in position in the left atrium 311. This set up may be employed to generate highly accurate pressure measurements because the number of variables affecting the measurements may be reduced. By measuring the pressure gradient across two locations, factors such as drift may be less of a problem as compared to conventional systems that measure the pressure gradient by referencing pressure measurements at each location to a vacuum. In addition, the combined left and right atrial information may be used to diagnose septal defects.

In one embodiment, the information generated by the leads may be provided to an external monitoring or control system. For example, the information may be provided to a stimulation device 100 as discussed herein. In addition, the stimulation device 100 may provide the information to another device such as the external device 254.

FIG. 4A is a diagram of one embodiment of an introducer catheter 400 (e.g., a sheath). In one embodiment, the introducer catheter 400 may have a proximal end with a housing 401. The catheter 400 may be formed of polyether block amide, high density polyethylene, silicone rubber, polyurethane or other materials. The materials used to form the catheter 400 may be biocompatible to prevent complication during insertion procedures.

In one embodiment, the housing 401 may be formed to couple to other devices or components. For example, the housing 401 may be formed to receive a dilator, needle, guidewire or similar component. The proximal end of the catheter 400 may also include openings to one or more lumens 407 within the catheter 400. The catheter 400 may contain any number of lumens. The lumens may run the length of the catheter or only run over a portion of the catheter 400. The lumens 407 may include a primary lumen.

The catheter 400 may have a diameter large enough to allow insertion of other components such as needles, leads, dilators and guidewires. The diameter may be small enough to enter and traverse the vascular system of a patient. In one embodiment, the diameter of the catheter may be 1-10 mm. The primary lumen 407 may have a diameter sufficient to receive a dilator, needle, guidewire or other components.

In one embodiment, the catheter 400 may be a deflectable catheter. The catheter may be manipulated to curve at its end to facilitate insertion. In a further embodiment, the catheter may be precurved. The catheter 400 may include a main body 405. The main body 405 may have any length. In one embodiment, the main body 405 has sufficient length to traverse an intravenous path to the right atrium of a heart. The housing 401 may include a mechanism 403 to control the distal end of the catheter 400 as it is advanced into a patient. The mechanism 403 may be a lever 403, control stick, handle or other mechanism to control the curve of the distal end of the catheter 400 using a wire line system or similar system. The distal end may contain or be covered with a marker 409 to assist in the insertion process. The marker 409 may be a heavy metal such as tantalum or similar substance that is visible via fluoroscopy or other systems for tracking instruments in a patient.

FIG. 4B is a diagram of one embodiment of a dilator 420. The dilator 420 may have a housing 421 at the proximal end, a long tubular body 427 and a distal tip 423. The dilator may be formed from silicon rubber, polyurethane, polyether block amide, high density polyethylene and other materials. The diameter of the dilator may be between 1-8 mm. In one embodiment, a portion of the dilator near the tip may have a larger outer diameter. In one embodiment, the length of the enlarged portion may be 5-8 mm. The length of a standard distal end 423 may be 1-5 mm.

In one embodiment, the housing 421 may be formed to connect to other components and provide access to one or more lumens 425 in the dilator 420. For example, the housing 421 may be designed to receive a needle, die injection device, guidewire or similar component. The set of lumens 425 may run the entire length of the dilator 420 or over a portion of the dilator 420. The lumens 425 may include a main lumen that runs a length of the dilator 420 and has a diameter sufficient to allow a needle, guidewire or similar structure to be inserted.

In one embodiment, the distal end 423 of the dilator 420 may have a tapered end. The distal end 423 may also have an opening to the main lumen 425. The opening may be of sufficient size to allow a needle, guidewire or similar structure to exit the distal end 423 of the dilator 420. In another embodiment, the distal end 423 may have an enlarged outer diameter before tapering to a point or opening. The enlarged section may be used to create a larger diameter hole in a wall, such as a septal wall, than was created by, for example, a piercing needle. The diameter of the hole may be increase by pressing the enlarged end of the dilator through the initially smaller opening in the wall. The enlarged end may also serve to temporarily lodge the dilator through a wall with a smaller opening.

FIG. 4C is a diagram of one embodiment of a needle 440. The needle 440 may have a proximal end 441 with an enlarged diameter. The proximal end 441 may be formed to be coupled to other instruments and devices. For example, the proximal end 441 may be coupled to a die injection device or similar device. The proximal end 441 may also include an opening to an interior lumen 443 or set of lumens. These lumens may run the entire length of the needle 440 or over a portion of the needle. The needle may be formed from a flexible material to allow it to follow the path of a dilator or catheter through a vascular system of a patient to the heart. In one embodiment, the needle 440 may be partially or fully formed from steel, Nitinol (an alloy of nickel and titanium), or another alloy or metal. In some embodiments, the needle may have a diameter of 0.25 to 5 mm.

In one embodiment, the distal end of the needle 440 may form a point 445. The point 445 may be sharp to puncture through organic structures. The end point 445 may also be open allowing access to the interior lumen 443. In another embodiment, the needle 440 may be solid with a solid tip 445.

FIG. 4D is a diagram of one embodiment of a guidewire 460. The guidewire 460 may be a single piece of wire with a proximal end 463 and distal end 461. The guidewire 460 may be a coiled steel wire, or similar wire. In one embodiment, the wire that forms the guidewire 460 may be a biocompatible material such as Nitinol, MP35N or other material. The proximal end 463 of the guidewire 460 may have an enlarged section or may be coupled to a handle or provide a similar gripping mechanism to facilitate manipulation of the guidewire 460. In one embodiment, the distal end 461 of the guidewire 460 may be a pointed, rounded, hooked or other shaped tip. In other embodiments, discussed below other specialized end structures may be utilized. The specialized end structures may be an integral part of the guidewire 460 or may be attached through welding or other techniques allowing the head (on the distal end 461) to be formed from a separate set of materials from the body.

FIG. 5A is a diagram of one embodiment of a lead 500 that includes a sensor 501 that may be implanted across a septal wall. The lead 500 may a flexible tube like structure with a diameter small enough to fit within a catheter. In one embodiment, the lead 500 may have a diameter between 1-10 mm. The lead 500 may be of any length. The lead 500 may have a length sufficient to reach the heart through a catheter inserted into a patient. The lead 500 may be primarily formed from polyurethane, silicone rubber, or other flexible biocompatible materials. In one embodiment, the lead 500 may be substantially formed from a single material.

In one embodiment, at a distal end of the lead 500 a sensor 501 is attached. The sensor 501 may be attached through adhesive or similar chemical bonding, form fit, snap fit, welding or any other attachment mechanism. The sensor 501 may be a fluid pressure sensor or similar sensor type. Example sensor types are discussed in greater detail below. The sensor 501 may be utilized to monitor pressure in the left side of the heart. The distal end may also include a marker 503 to allow monitoring of the position of the lead tip in the body of the patient. For example, the marker 503 may be a heavy metal that is visible through fluoroscopy.

In one embodiment, the lead 500 may include one or more lumens. The set of lumens may include a guidewire lumen 505. The guidewire lumen 505 may run the length of the lead 500. A guidewire may be inserted into the lumen or the lead may be threaded over the guidewire. The guidewire lumen 505 may be accessible from an opening in the tip (at the distal end) of the lumen 505 and in a proximal housing 513 of the lead 500. The proximal housing may also include a clamping or attachment mechanism 507. The clamping mechanism may be used to attach or fix the lead 500 in relation to the guidewire. For example, the clamping mechanism may include a screw that passes through the line of the guidewire lumen 505 to press the guidewire against an inner wall of the lumen 505 or against a wall of a recessed region opposite the screw. This fixes the guidewire in place relative to the lead 500.

In one embodiment, the set of lumens may include a primary lumen (not shown) that provides a space for a set of electrical conductors to connect with the sensor 501. The primary lumen may run the length of the lead and have a proximal end that is in the form of a connector or that is coupled to an extension of the lumen at proximal housing 513 that allows coupling to an external device. A set of electrical connectors may be present at the proximal end of the lumen. A male-female coupling attachment or similar attachment mechanism may be combined with the electrical connectors to enable the sensor 501 to be in electrical communication with an external device.

In one embodiment, the proximal end 511 of the lead may be formed as a coupling mechanism to attach the lead 500 to an implantable device For example, the implantable device may be a monitoring device that collects information from the lead sensor 501 and a stimulation device that generates an electrical pulse to stimulate the heart through an electrode implanted with the lead 500 or as part of the lead 500. In this example, the lead 500 may have a set of electrodes in the tip that are in contact with the septal wall when the lead 500 is in place. This set of electrodes can be used to induce an electrical current or pulse to the heart for use in pacemaker type applications.

FIG. 5B is an end view of one embodiment of the lead 500. The sensor 501 may have a circular, ovoid or other shape to fit through a passage formed in a septal wall of the heart by a needle. The tip includes an opening 515 to the guidewire lumen. The guidewire may be threaded into this opening or exit this opening when inserted at the proximal end.

FIG. 6A is a diagram of one embodiment of a specialized guidewire 600 that may be used to mount a lead (e.g., lead 500) to a septal wall. The specialized guidewire 600 may be a flexible integral piece of metal, alloy, plastic or other flexible material. In another embodiment, the guidewire may have sections of different materials that are welded together or otherwise attached to one another. For example, the guidewire may have a steel body and a head portion 603 that is formed from another material such as Nitinol.

The guidewire 600 may have a specially shaped head region 603. For example, the guidewire head 603 may have a spiral, ovoid, circular, rectangular or other shape. The footprint of the head 603 may be large compared to the guidewire 600 and as large as the diameter of the lead or larger than the diameter of the lead. The head region 603 may be used to clamp down on the septal wall in conjunction with the end of the lead. The proximal end of the guidewire 600 may be secured to the lead to maintain the relative position of the guidewire 600 in relation to the lead and to maintain the clamp or mounting of the sensor in the left atrium of the heart. The guidewire 600 may be secured through a securing mechanism 513 such as a clamp type mechanism, screw mechanism or other securing mechanism.

In one embodiment, the guidewire 600 may be formed of a conductive material. The conductive guidewire 600 may be used to induce an electrical pulse to the heart for sensing or stimulation functionality.

FIG. 7A is a diagram of another embodiment of a lead 700 that includes a sensor 705 that may be implanted across a septal wall. In one embodiment, the proximal end 701 of the lead may be formed as a coupling mechanism to attach the lead 700 to an implantable device. As discussed above, the coupling mechanism may be a male-female connector or similar connector. The coupling mechanism may include a set of electrical contacts that electrically couple the implantable device to the lead including the sensor 705.

In one embodiment, the distal end of the lead 700 includes a sensor 705 and a mounting mechanism 703. The sensor 705 may be a pressure sensor or other sensor device. The sensor 705 may provide left chamber pressure information to an external monitoring device.

FIG. 7B is a cross section diagram of an enlarged view of one embodiment of a mounting mechanism 703 and sensor 705 of a lead 700. In one embodiment, the mounting mechanism includes a spring 707 and a set of tines 711. The spring 707 is housed in an interior compartment 717 of the end of the lead 700. The interior compartment 717 may be annular in shape. The outer walls 715 of the annular compartment and lead 700 are flexible in the area of the outer walls 715. The end of the lead 700 also has a stiff circular or ovoid section 709 that forms an end cap for lead 700 and interior compartment 717. The stiff section 709 slides in relation to an inner core 719 of the lead 700. If pressure is applied to the stiff section 709 the stiff section 709 slides in a proximal direction compressing the spring 707 and flexing the outer walls 715.

In one embodiment, the inner core 719 extends beyond the larger portion of the lead 700 and houses at least a portion of the sensor 705 and a guidewire lumen 713. The guidewire lumen 713 may run over the length of the lead 700. The extended section of the inner core 719 may also have a set of extending tines 711 attached near the tip. Any number of tines 711 may be provided. In one embodiment, three or more tines 711 are provided. The tines 711 may be equally spaced and provide a footprint to press against a septal wall. In some embodiments, the tines 711 are positioned a given distance apart on the tip. The tines 711 maybe spaced apart at a distance approximately equal to the thickness of the septal wall in the area of the implant. For example, the distance apart may be 5-4 mm.

In one embodiment, the tines 711 may be flat strips of metal, metal alloy, silicone, polyurethane, plastic or similar resilient materials. In another embodiment, the tines 711 may be formed from biodegradable material. This type of material may be used, for example, in a case where it may be necessary to remove the lead after implantation. The tines 711 may fold against the body of the interior core 719 during insertion into the patient through the catheter. The tines 711 may expand in the left chamber of the heart after the extended portion of the interior core 719 passes through the catheter and the hole in the septal wall. The space between the base of the tines 711 and the stiff portion 709 may be small enough to press against each side of the septal wall once inserted through the septal wall. The space between the base of the tines 711 and the stiff member 709 in its natural position may be slightly small than the typical thickness of the septal wall or fossa ovalis. In one embodiment, the width of this space may be tailored to width of the septal wall of each individual patient.

In one embodiment, the spring mechanism 707 may maintain the pressure on the septal wall and pull the tines 711 flat against the septal wall to maintain a low profile for the tines 711 and sensor 705. For example, spring mechanism 707 may force the tines 711 to press against a septal wall in the left side of the heart and force the end of the stiff portion 709 to press in an opposite direction against the opposite septal wall on the right side of the heart.

The spring mechanism may be a metal spring or spring made from other materials with strong material memory. The spring may be MP35N, nickel chrome alloys or other biocompatible materials.

In another embodiment, a separate spring structure may not be present. The outer walls 715 may be formed with materials or structure with a memory and resiliency equivalent to a separate spring structure. The outer walls 715 would thus function as a spring to pull the tines 711 into place when deployed.

A variety of tines or tine like structures may be used in embodiments of the mounting mechanism. For example, any number of tines or tine like protrusions may be used in each set of tines discussed herein. The tines may be configured to be extendable and retractable. The tines may have a retracted or compressed position within the body of the lead 700. In one embodiment, the tines may also be electrically connected and function as electrodes to deliver electrical pulses to the septal wall.

Figure 8:
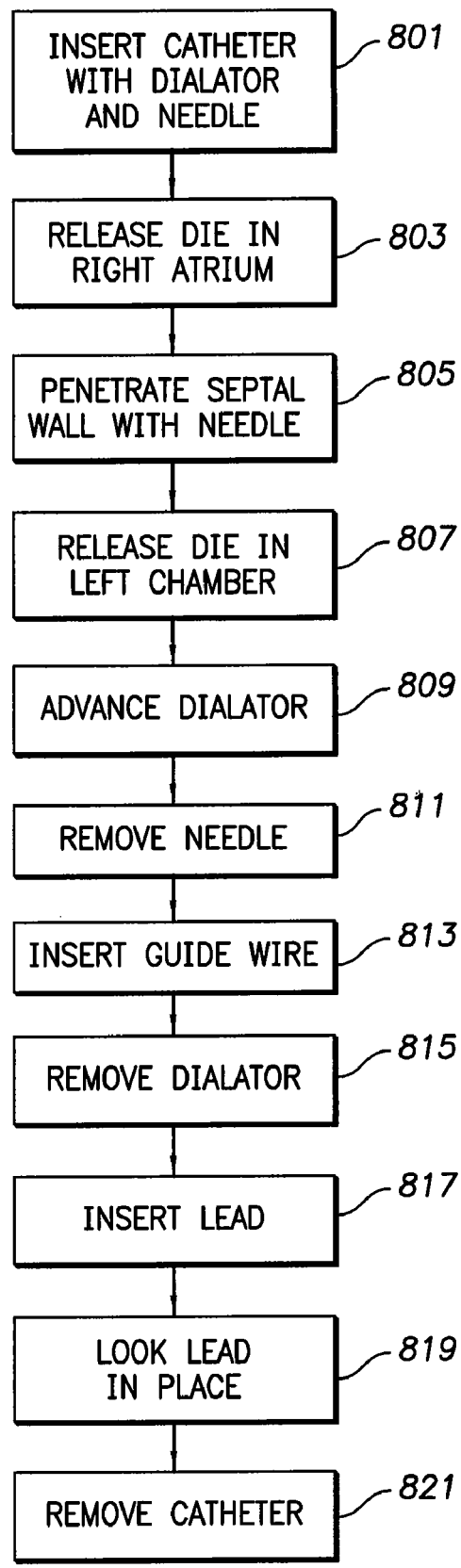
FIG. 8 is a flowchart of one embodiment of a process for inserting a lead.

FIG. 8 is a flowchart of one embodiment of a process for installing a lead and pressure sensor in the left atrium to monitor pressure in the left atrium. The described process is presented as an example. It should be understood that the teachings herein also may be used to measure pressure in other areas such as the left ventricle. FIGS. 9-17 serve to illustrate the process and will be referred to as part of the discussion of the process.

In one embodiment, the process of implanting the sensor begins by the placement of the catheter into the patient. The distal end of the catheter is placed into the right atrium of the patient using known techniques. The distal end of the catheter may be positioned adjacent the septal wall and the fossa ovalis. In one embodiment, after the catheter is in position a dilator and needle may be inserted into the catheter (block 801). In another embodiment, the needle alone may be inserted at this time and the dilator may be inserted over the needle at a subsequent time.

In one embodiment, once the needle and dilator are in place with the distal tips of each of the needle and dilator in the right atrium a die may be released to detect or confirm the location in the heart of the catheter, needle and dilator (block 803). The die may be used in connection with fluoroscopy or similar techniques and systems for monitoring instrument position in the body of a patient.

In one embodiment, with the location of the needle known in the right atrium, the needle may be repositioned, if necessary, and advanced to penetrate the septal wall at the fossa ovalis (block 805). The release of die or use of other markers may continue through the process of penetration or may be restarted just after penetration of the septal wall (block 807). The release of the die allows for confirmation of the penetration of the septal wall through fluoroscopy or similar systems. Also, the die released in the right atrium prior to penetration may flow through the puncture and indicate that the septal wall has been penetrated. Thus, the process may involve releasing die in the left atrium.

Figure 9:
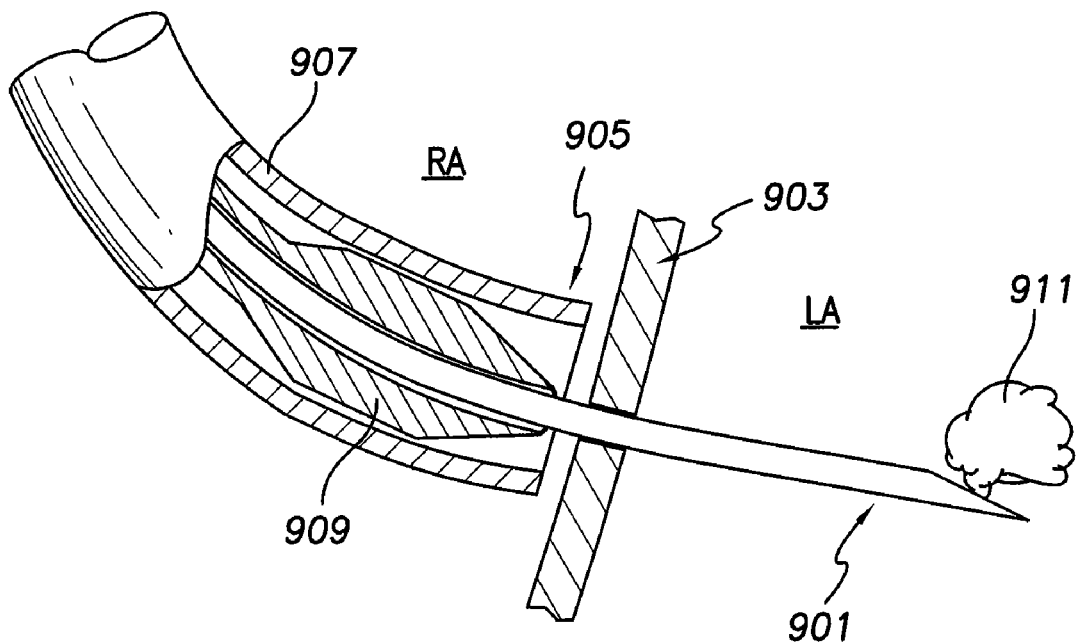
FIG. 9 is an illustration of a partial cut-away view of one embodiment of a needle piercing a septal wall.

FIG. 9 is a diagram illustrating the penetration of the septal wall 903 by a needle 901. The needle 901 has been advanced through the septal wall 903. The position of the catheter 907 in the right atrium ("RA") may be tracked by the marker tip 905. At this point the dilator 909 remains within the catheter 907 until the penetration of the septal wall 903 is confirmed by detecting the die 911 in the left atrium ("LA"). In one embodiment, the dilator 909 may have a tapered end and an enlarged portion that has a larger diameter than the main body of the dilator.

Figure 10:
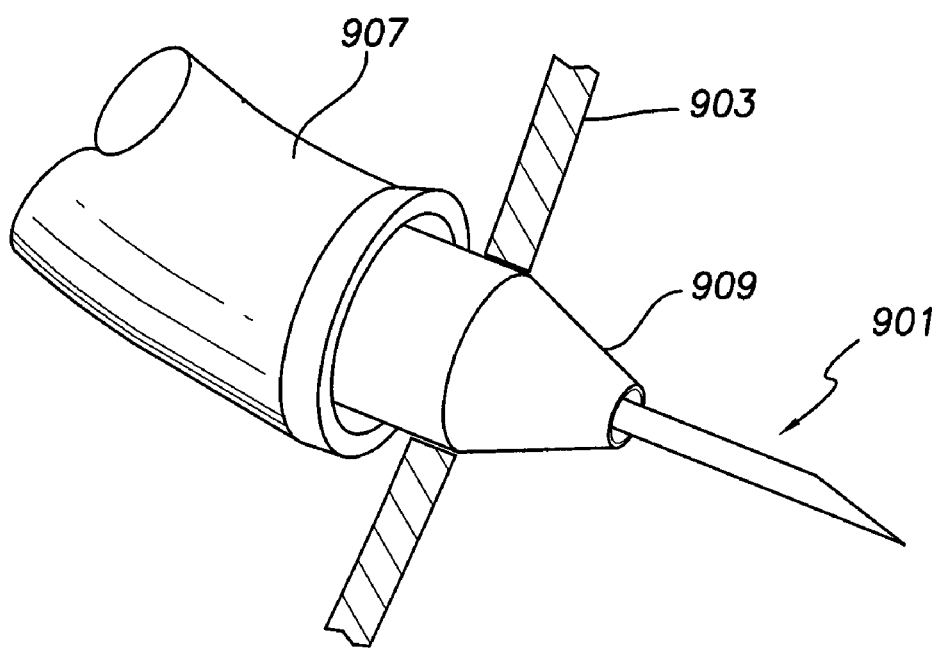
FIG. 10 is an illustration of one embodiment of a dilator inserted into a septal wall

In one embodiment, after it has been confirmed that the needle successfully penetrated the septal wall, the dilator may be advanced through the opening created by the needle (block 809). FIG. 10 is a diagram illustrating the advancement of the dilator 909. The needle 901 remains in place to guide the advancement of the dilator 909. In one embodiment, the enlarged head of the dilator 909 may be advanced to enlarge the hole in the septal wall and lodge the dilator in the hole. In another embodiment, the enlarged portion of the dilator 909 may be advanced through the hole in the septal wall 903 to partially anchor the dilator into place.

Figure 11:
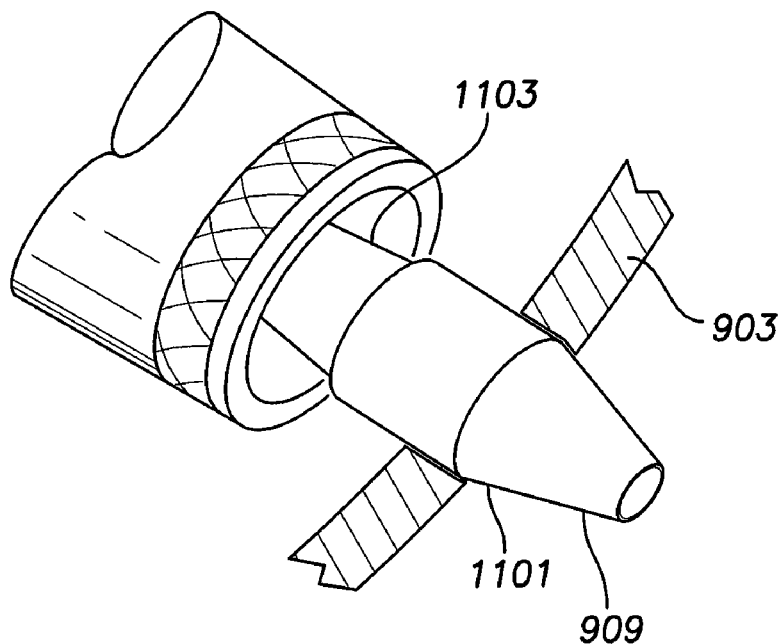
FIG. 11 is an illustration of one embodiment of a dilator after a needle is removed.

In one embodiment, after the dilator is in place the needle may be removed from the patient and from the catheter (block 811). FIG. 11 is a diagram illustrating a potential position of the dilator 909 at the time the needle is removed. An enlarged head 1101 of the dilator 909 is positioned just inside the left atrium. The dilator 909 may maintain its position if a moderate pulling force is applied, but can be removed without damaging the septal wall 903.

FIG. 11 illustrates one embodiment where the enlarged head 1101 of the dilator 909 has a larger diameter than a main body 1103 of the dilator 909. Such a configuration may enable the dilator 909 to be more easily maneuvered (since the body 1103 is smaller) while still providing a relatively large hole (since the head 1101 is larger) in the septal wall 903. In addition, such a configuration may serve to temporarily prevent the dilator 909 from being dislocated from the septal wall by a moderate force in the proximal direction. For example, the dilator 909 may be positioned further into the left atrium such that the smaller main body 1103 passes through the septal wall 903. Here, the larger head 1101 may provide some resistance to a force in the proximal direction. This may prove advantageous, for example, when removing the needle from the dilator 909 or inserting a guidewire into the dilator 909.

Figure 12:
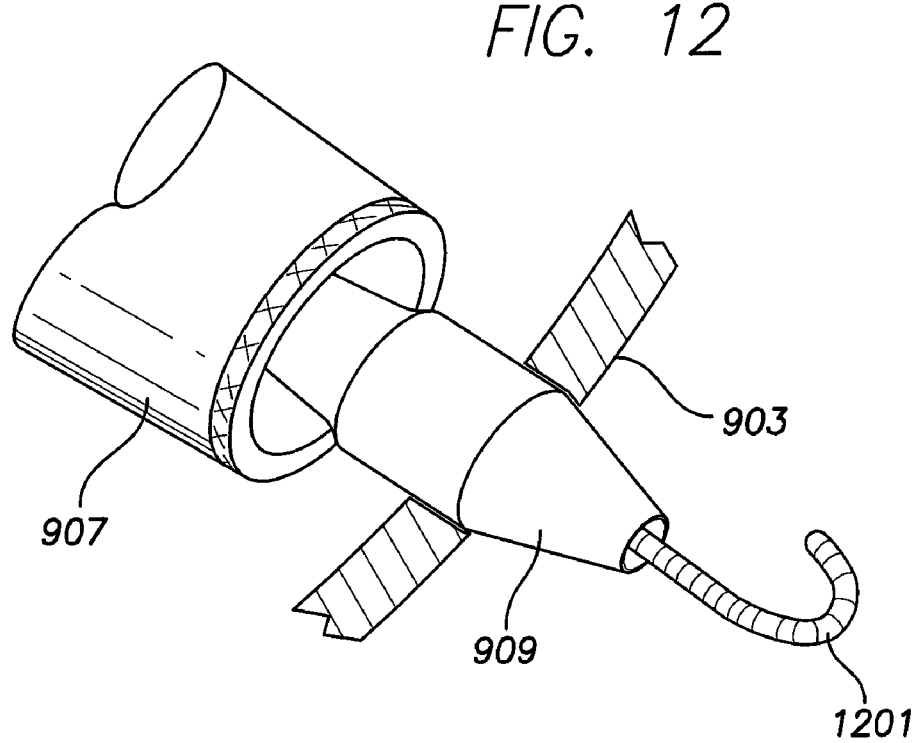
FIG. 12 is an illustration of one embodiment of a guidewire inserted through a dilator.

In one embodiment, after the needle has been removed, a guidewire may be inserted in preparation for insertion of a lead (block 813). FIG. 12 is a diagram illustrating one embodiment of the insertion of a guidewire 1201. The guidewire 1201 may be threaded through the dilator 909 and catheter 907 and into the left atrium of the heart. The tip of the guidewire 1201 may have a marker or may be formed from a metal or alloy that functions as a marker in a system such as fluoroscopy.

Figure 13:
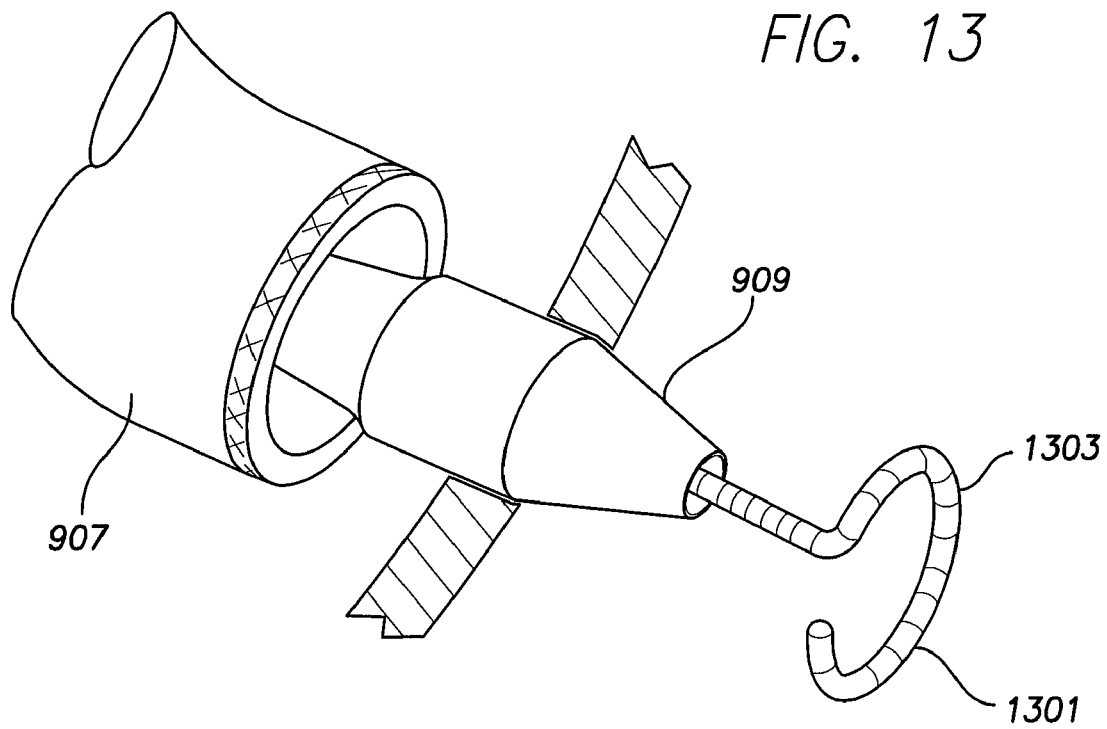
FIG. 13 is an illustration of one embodiment of a guidewire inserted through a dilator.

FIG. 13 is a diagram of an embodiment with a specialized guidewire 1301. The specialized guidewire may be threaded down the catheter 907 or dilator 909 into the left atrium. The head portion 1303 of the specialized guidewire 1301 may be formed from a flexible material allowing it to be bent or compressed into the dilator 909 or catheter 907. When the head portion emerges from the dilator or catheter 907 into the left atrium of the heart, the head portion 1303 returns to its natural shape embedded in the memory of the material of the head. For example, the head portion 1303 may revert to the shape of a spiral. The head portion 1303 may have a marker on it or may be formed from a material that functions as a marker.

Figure 14:
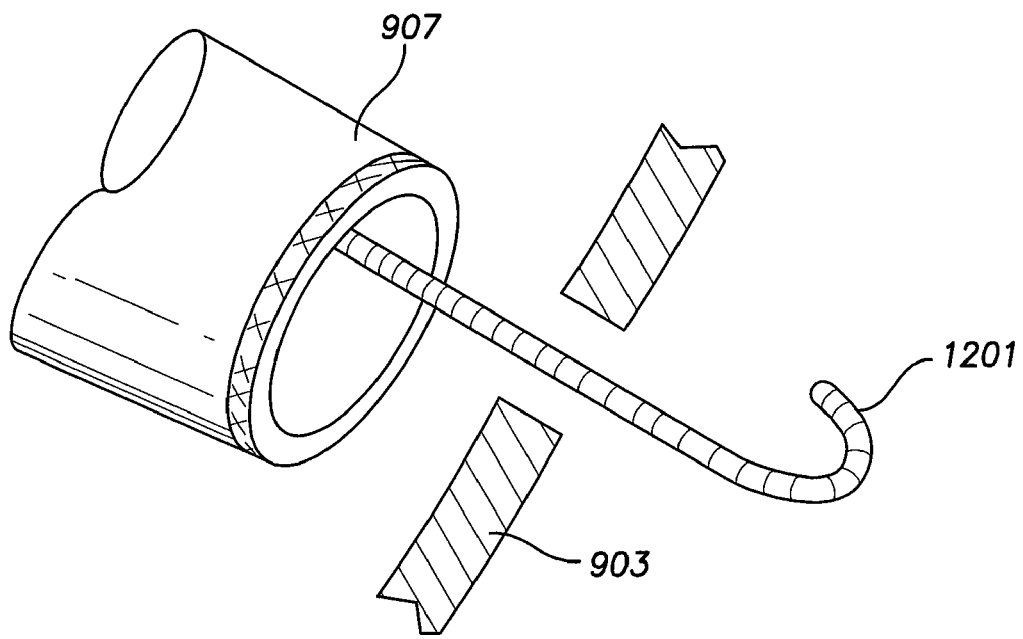
FIG. 14 is an illustration of one embodiment of a guidewire after a dilator is removed.
Figure 15:
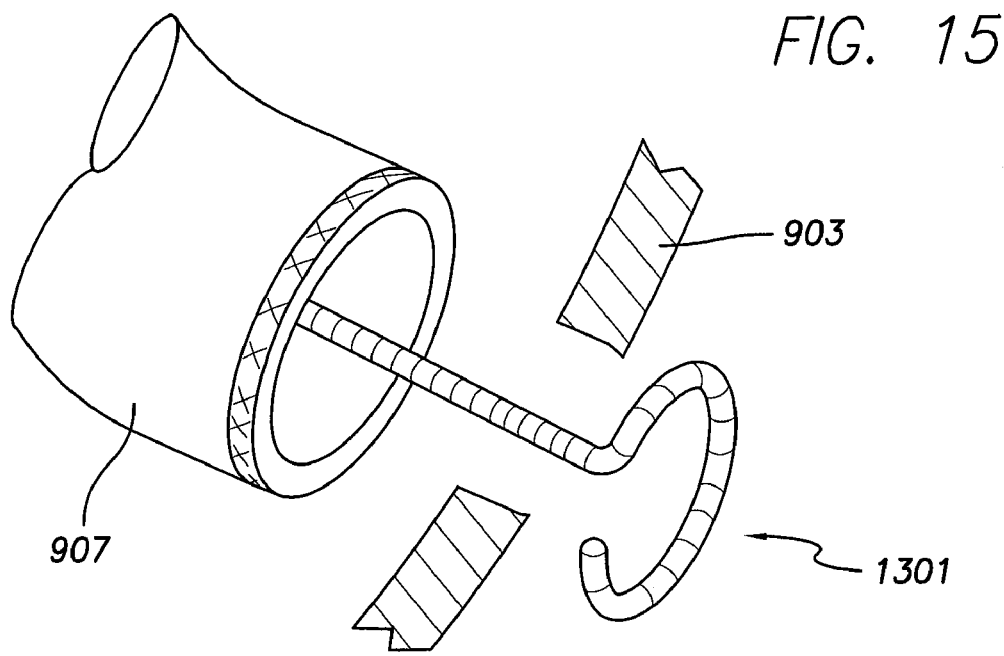
FIG. 15 is an illustration of one embodiment of a guidewire after a dilator is removed.

In one embodiment, after the guidewire is confirmed to be in place, the dilator may be removed (block 815). The dilator may be pulled out through the catheter without moving the guidewire. FIGS. 14 and 15 are diagrams illustrating the position of two types of guidewires after the removal of the dilator. The end of each guidewire 1201, 1301 remains in the left atrium, unaffected by the removal of the dilator. For example, a tension may be maintained on the guidewire 1201, 1301 as the dilator 900 is withdrawn. The catheter 907 also remains in position in the right atrium. For example, a tension may be maintained on the catheter 907 to keep it pushed against the septal wall 903.

In one embodiment, after the dilator 909 has been removed, a lead may be inserted into the patient (block 817). The lead may be threaded over the guidewire to lead it to the hole in the septal wall where the sensor at the tip of the lead is to be inserted. The lead includes a lumen into which the proximal end of the guidewire is inserted. The guidewire may be significantly longer than the section necessary to traverse the length of the catheter. The guidewire may be threaded through the entire lead before insertion of the lead into the catheter without disturbing the distal end of the guidewire in the left atrium. This way the guidewire can still be held in place while the lead is advanced through the catheter.

In one embodiment, after the lead has been advanced into place in the right atrium or with the sensor in the left atrium, the mounting mechanism is set to maintain the position of the sensor in the left atrium and to minimize the profile of the sensor (block 819). The mounting mechanism is positioned against the wall in a manner that may prevent the lead and sensor from moving relative to the wall. In this way, the mounting mechanism serves to effectively hold the lead and sensor in the proper position.

Figure 16:
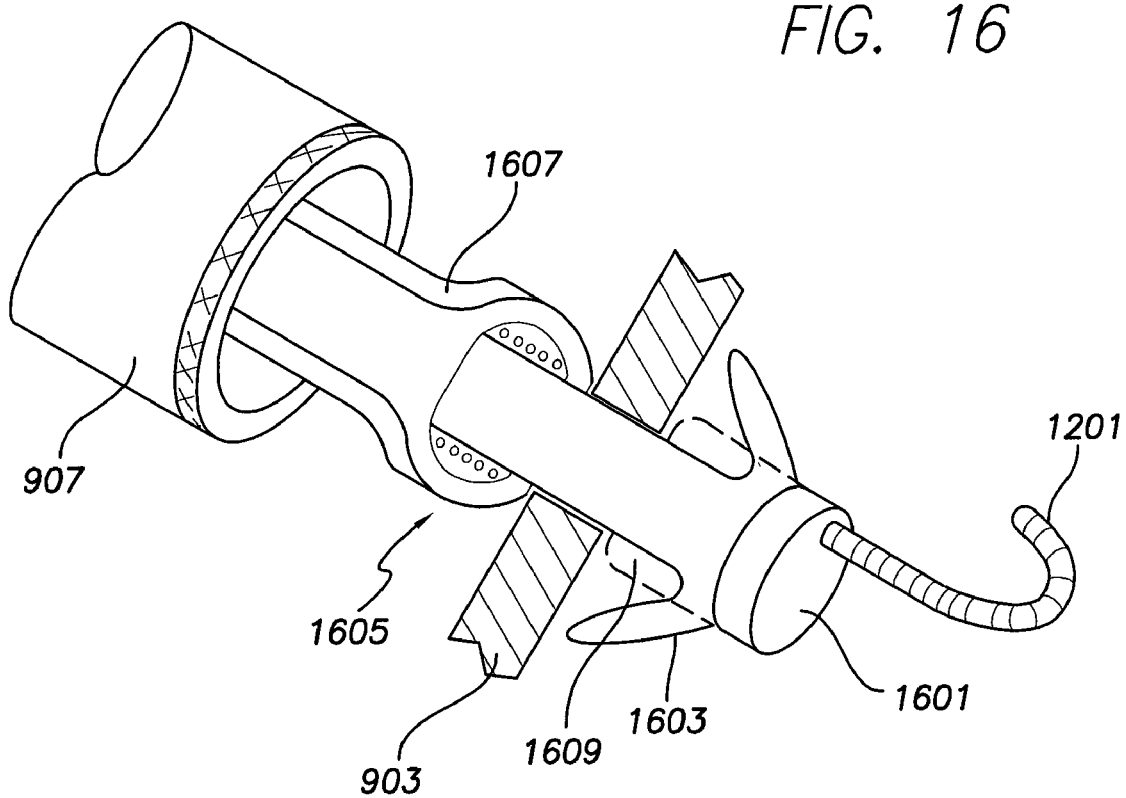
FIG. 16 is an illustration of one embodiment of a lead inserted into a hole in a septal wall.

FIG. 16 is a diagram of one embodiment of a mounting mechanism and sensor for a lead 1607. In this example, the lead 1607 has been advanced into the right atrium and the tip has been placed through the hole in the septal wall 903 by following the guidewire 1201. The tip of the lead 1607 includes a sensor 1601 and a set of tines 1603. The tines 1603 are collapsible against the body of the lead 1607. When the tip of the lead 1607 is advanced through the catheter 907 and septal wall the tines 1603 are partially or completely flattened (as represented by the dashed lines 1609) against the lead 1607.

In one embodiment, a base portion of the tip includes a compressible or biasing mechanism 1605. The biasing mechanism 1605 has a wider dimension than the hole in the septal wall 903. As the tip of the lead 1607 is advanced through the hole, the biasing mechanism begins to compress against the septal wall. The biasing mechanism 1605 exerts a force against the septal wall 903 that may be overcome by the force of the advancement of the lead 1607.

Figure 17:
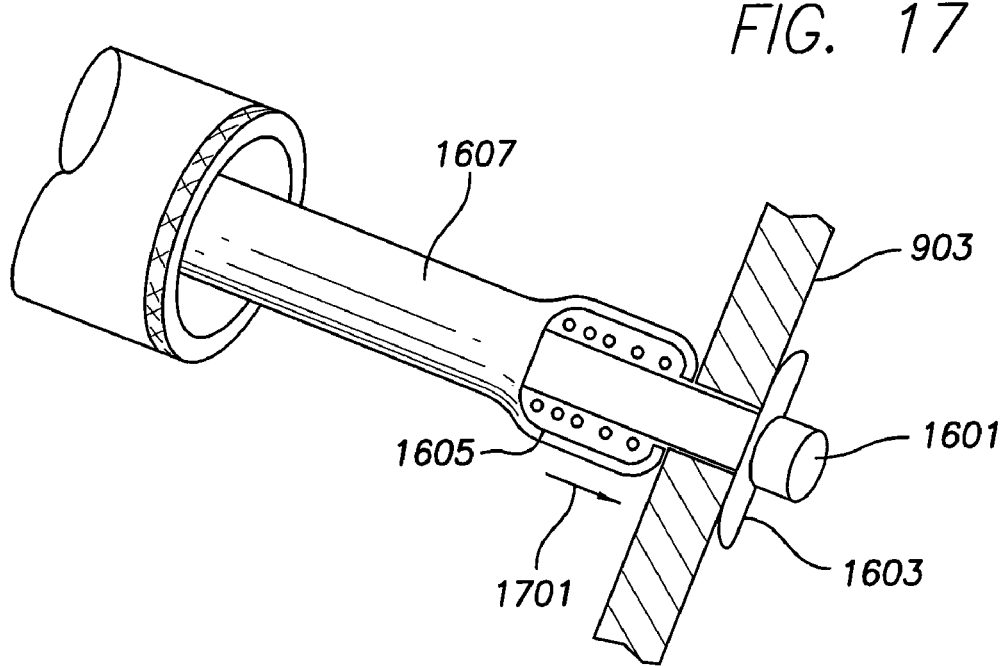
FIG. 17 is an illustration of a partial cut-away view of one embodiment of a lead secured in a septal wall.

FIG. 17 is a diagram of the lead 1607 in a final position in the septal wall 903. After the tip of the lead 1607 including the tines 1603 is completely within the left atrium the force (as represented by the arrow 17 01) advancing the lead 1607 may be relaxed. The biasing mechanism 1605 pushes against the septal wall 903 back to its natural position. This pulls the tines 1603 on the other side of the septal wall 903 flat against the wall and lowers the profile of the sensor 1601 in the left atrium.

Figure 18:
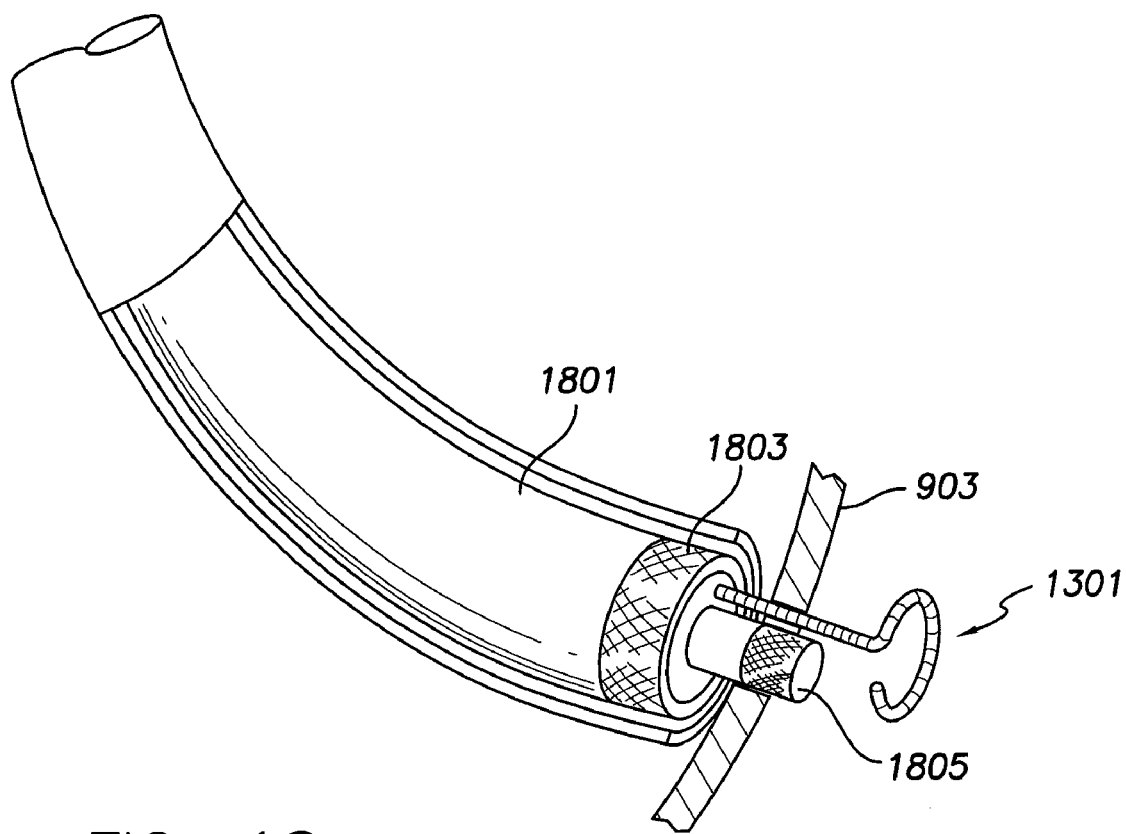
FIG. 18 is an illustration of a partial cut-away view of one embodiment of a lead and guidewire secured through a septal wall.

FIG. 18 is a diagram of another embodiment of a mounting mechanism for a lead 1801. The lead 1801 is advanced into place with the tip including a sensor 1805 positioned through the septal wall 903. Once the tip of the lead 1801 is in place the guidewire 1301 is retracted slightly to press against the septal wall 903, bringing a base 1803 of the lead end up against the other side of the septal wall 903. When the septal wall is securely clamped between the base 1803 and the guidewire 1301 then the proximal end of the guidewire 1301 may be fastened to the lead 1801 to fix the relative position of the lead 1801 and the guidewire 1301 to secure the end of the lead 181 and sensor 1805 in their positions.

Figure 19A:
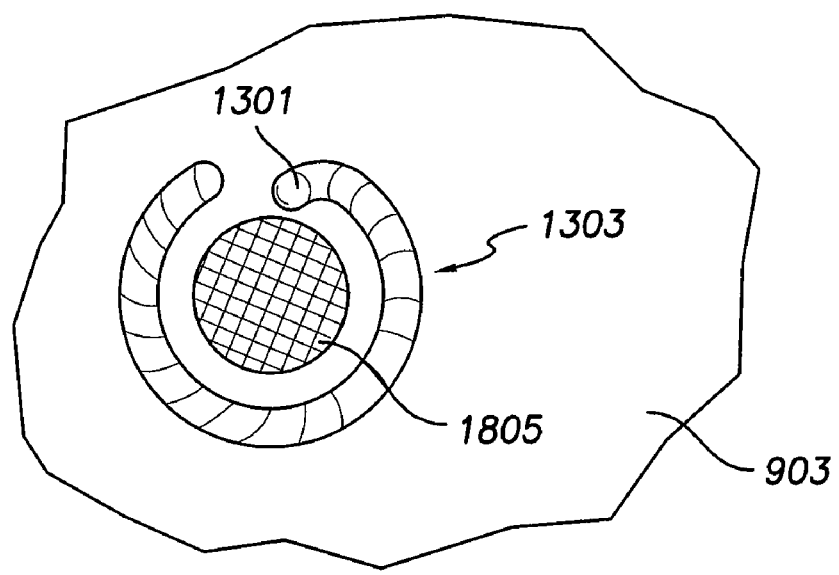
FIG. 19A is a diagram of one embodiment of a guidewire head.

FIG. 19A is a diagram of an end view of one embodiment of a head of the specialized guidewire 1301. In one embodiment, the head 1303 of the guidewire has a roughly circular shape. The shape of the head arcs outward to create a sizable footprint to allow the guidewire to press a section of the septal wall 903 against the body of the lead when the guidewire 1301 is pulled taught. In this embodiment, the guidewire is designed to remain in the patient as part of the mounting mechanism.

Figure 19B:
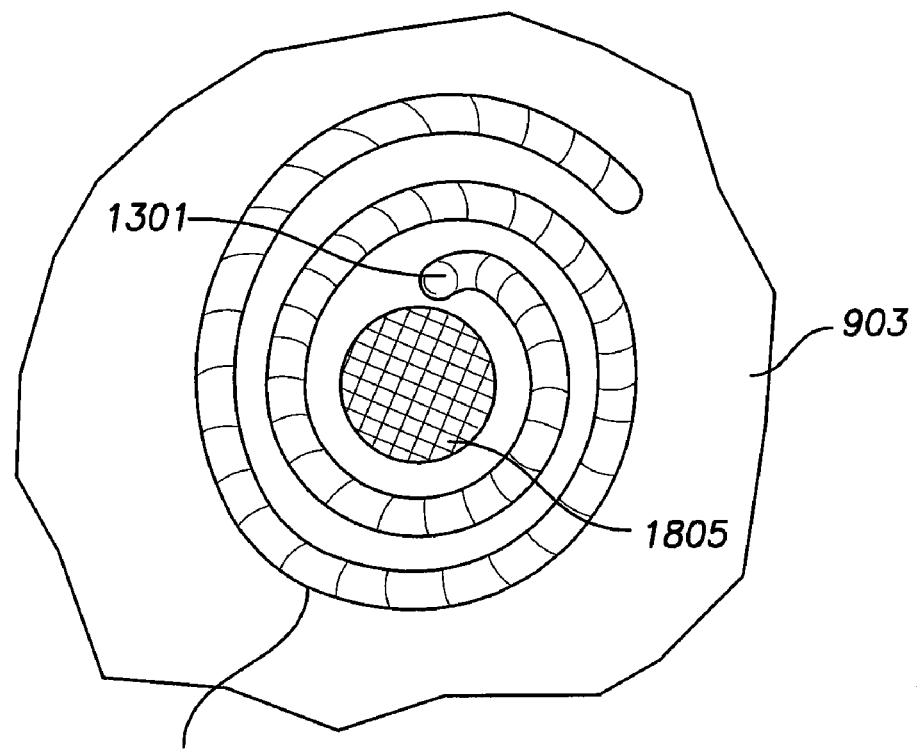
FIG. 19B is a diagram of one embodiment of a guidewire head.

FIG. 19B is a diagram of another embodiment of the specialized guidewire 1301. The guidewire 1301 may have a larger or more complex shape to the head portion 1303. In one embodiment, the head portion has a spiral shape. The shape and size may be designed to increase the footprint of the head portion 1303 to secure the guidewire 1301 and the sensor 1805 in place.

In one embodiment, after the mounting mechanism has been set, the catheter may be removed (block 821) from the patient leaving the lead and in some embodiments leaving the guidewire in place (e.g., the embodiment of FIG. 18). The catheter may be a peelable catheter allowing the catheter to be easily removed without disturbing the lead and its connections. In one embodiment, the catheter may have a weakened area or wick along the length of the catheter to facilitate its removal. In another embodiment, the catheter may be cut off or similarly separated from the lead.

Figure 20:
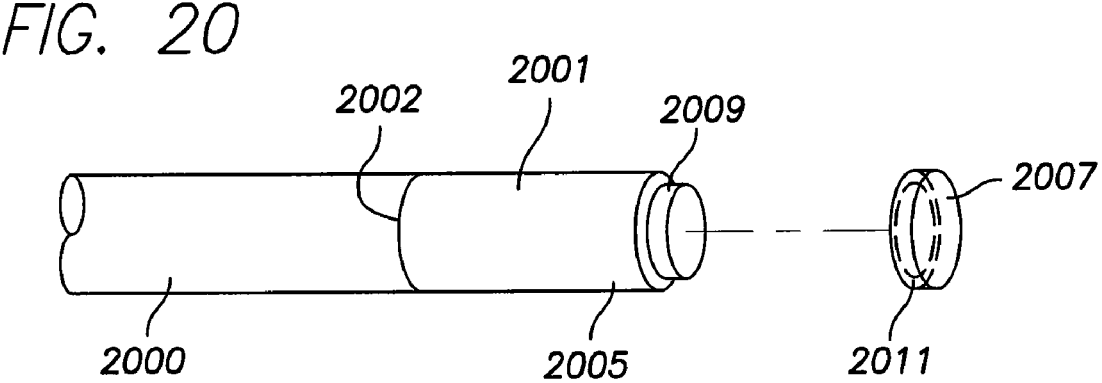
FIG. 20 is a diagram of one embodiment of a sensor attached to an end of a lead.

FIG. 20 depicts one embodiment of a sensor mounted on the distal end of a lead 2000. In this example, a sensor 2001 is attached to an end of a lead body 2003. Typically, the sensor 2001 and the lead body 2003 would have the same diameter. Thus, they may be configured in a co-circumferential orientation. The sensor 2001 may be attached to the lead body 2003 by a variety of techniques including, for example, laser welding and adhesive attachment (e.g., using an epoxy).

In one embodiment, the sensor 2001 may include a flexible diaphragm 2007 at its distal end. The sensor case 2005 and flexible diaphragm 2007 are shown in an exploded view to illustrate one technique for attaching the flexible diaphragm 2007 to the sensor case 2005. Specifically, the flexible diaphragm 2007 may be formed with a lip that is placed over a seat provided on the end of the sensor case 2005. Thus, an inside surface 2011 of the lip may, for example, be adhered to an outside surface 2009 of the seat. The lip of the flexible diaphragm 2007 may be attached to the seat of the sensor body using a variety of techniques including, for example, laser welding and adhesive attachment (e.g., using an epoxy).

In general, various aspects of the sensor may be constructed using known materials and techniques. For example, the sensor case may be constructed of a variety of materials including, for example, titanium or other biocompatible metals and materials. The sensor may include a pressure-to-electrical transducer such as a piezo electric chip. One or more electrical conductors may be routed out the proximal end of the sensor 2001 through the lead 2000 to connect the sensor 2001 to an implantable device (not shown in FIG. 20).

The interior of the sensor case 2005 may be filled with a biocompatible fluid or gel such as, for example, silicone oil. A port may be provided in the sensor case to facilitate filling the interior with fluid and for removing bubbles from the fluid. A plug mechanism such as a screw may be used to close the port.

Figure 21:
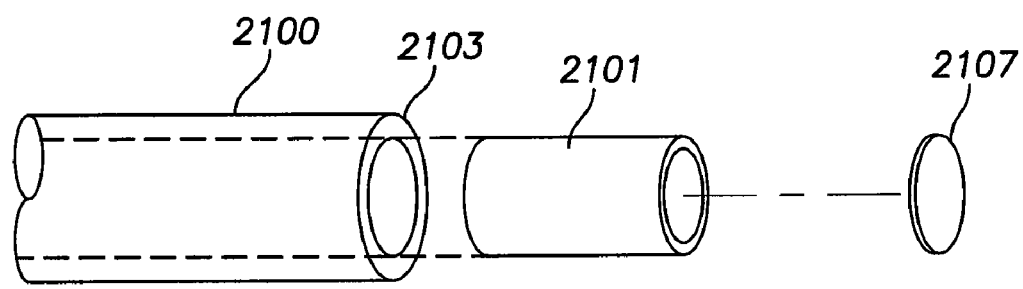
FIG. 21 is a diagram of one embodiment of a sensor attached to a lead internally.

FIG. 21 depicts an embodiment of a lead 2100 where a sensor 2101 is inserted into a distal end of a lead body 2103. The sensor 2101 includes a flexible diaphragm 2107 on its distal end. The lead body 2103 and sensor 2101 are shown in an exploded view to illustrate how these components may be assembled.

In one embodiment, the sensor 2101 is inserted into the lead body 2103. In this case, an outside surface of the sensor 2101 may be affixed to an inside surface of the lead body 2103. Typically, the sensor 2101 will be fully inserted into the lead body 2103. Thus, the distal ends of the lead body 2103 and the sensor 2101 (e.g., the flexible diaphragm 2107) may be aligned. In this case the mounting mechanisms (not shown) may be attached to or built into the lead body 2103.

Figure 22:
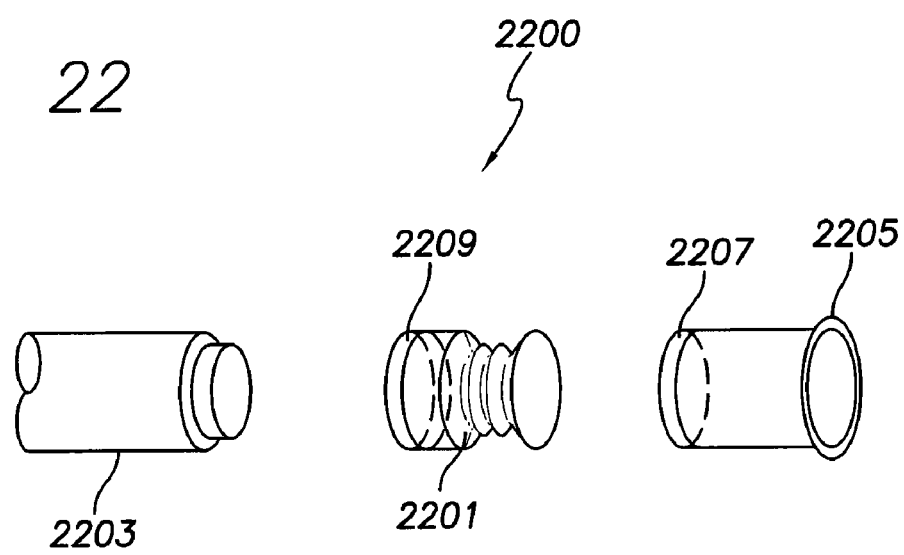
FIG. 22 is a diagram of one embodiment of the components of the sensor.

FIG. 22 depicts one embodiment of an exploded view of one embodiment of a sensor 2200 incorporating a flexible bellow 2201. A main sensor housing 2203 incorporates a pressure-to-electrical transducer that generates electrical signals provided to an electrical conductor.

The main sensor housing 2203 also includes a seat adapted to receive a base portion of the bellow 2201. An inside surface of the base portion may, for example, be adhered to an outside surface of the seat using a variety of techniques including, for example, laser welding and adhesive attachment (e.g., using an epoxy).

The distal end of the bellow comprises a wall or end piece that forms the distal end of the sensor assembly 2200. The interior of the bellow 2201 and the main housing 2203 may then be filled with a non-compressible fluid.

In some embodiments, the sensor 2200 may include a bellow cover 2205. The bellow cover 2205 may facilitate attaching the sensor 2200 to a lead. For example, a mounting mechanism such as tines may be affixed to the outside of the bellow cover 2205. In addition, the bellow cover 2205 may include a lip to which a mounting mechanism may be attached.

A base portion 2207 of the bellow cover 2205 may be adapted to be affixed to the base portion 2209 of the bellow 2201. An inside surface of the base portion of the bellow cover 2205 may, for example, be adhered to an outside surface of the base using a variety of techniques including, for example, laser welding and adhesive attachment (e.g., using an epoxy).

In operation, changes in pressure in the left side of the heart will cause a distal surface of a bellow 2201 in the sensor 2200 to move. In general, the bellow 2201 may expand and contract in relation to the fluid pressure.

In view of the above, it should be understood that a lead may be constructed using various combinations and modifications of the structures and components described herein. For example, the structure and components described in a given drawing may be used in a lead described in another drawing. In addition, lead components such as sensors, electrodes, mounting mechanisms such as tines may be located at various locations on the lead.

In addition, the structures described herein may be implemented in a variety of ways. For example, the leads described herein may be formed by attaching various components together. Also, the combinations of some of the components which are described herein as being "attached," "connected" "including," "affixed," etc., may be implemented as one or more integral components.

It should be appreciated that the applications discussed herein regarding various embodiments may be applicable to other uses and contexts as well. For example, the leads described above may be implanted across any wall including the atrial septum and/or the ventricular septum. Different embodiments of the external monitoring and control systems described above may include a variety of hardware and software processing components. In some embodiments of the invention, hardware components such as controllers, state machines and/or logic are used in a system constructed in accordance with the invention. In some embodiments, code such as software or firmware executing on one or more processing devices may be used to implement one or more of the described operations. The signals between sensors and external devices may take several forms. For example, in some embodiments a signal may be an electrical signal transmitted over a wire while other signals may consist of wireless signals transmitted through space. In addition, a group of signals may be collectively referred to as a signal herein. The signals discussed above also may take the form of data. For example, in some embodiments an application program of an external device may send a signal to another application program. Such a signal may be stored in a data memory.

In summary, the invention described herein may be used as part of an improved cardiac pressure sensing apparatus. While certain exemplary embodiments have been described above in detail and shown in the accompanying drawings, it is to be understood that such embodiments are merely illustrative of and not restrictive of the broad invention. In particular, it should be recognized that the teachings of the invention apply to a wide variety of systems and processes. It will thus be recognized that various modifications may be made to the illustrated and other embodiments of the invention described above, without departing from the broad inventive scope thereof. In view of the above it will be understood that the invention is not limited to the particular embodiments or arrangements disclosed, but is rather intended to cover any changes, adaptations or modifications which are within the scope and spirit of the invention as defined by the appended claims.

What is claimed is:

1. A method of implanting a sensor in a first chamber of a heart, said method comprising:

placing a guidewire through a hole formed in a septal wall separating the first chamber from a second chamber of the heart, the septal wall having a first side forming the first chamber and a second side opposite the first side and forming the second chamber;

passing a lead over the guidewire, the lead having a longitudinal axis and an inner core with a distal end, the distal end carrying the sensor and a set of collapsible tines, the lead further comprising a biasing mechanism proximal the sensor and tines and configured to compress and expand along the longitudinal axis of the lead;

applying a force along the axis of the lead to thereby advance the sensor and tines through the hole into the first chamber, and compress the biasing mechanism against the second side of the septal wall; and after the sensor and the tines are in the first chamber, relaxing the force along the axis to thereby allow the biasing mechanism to bias against the second side of the septal wall and the tines to expand and press against the first side of the septal wall.

* * * * *